US009310381B2

(12) United States Patent
Donnenberg

(10) Patent No.: US 9,310,381 B2
(45) Date of Patent: *Apr. 12, 2016

(54) ENGINEERED TYPE IV PILIN OF CLOSTRIDIUM DIFFICILE

(71) Applicant: University of Maryland, Baltimore, Baltimore, MD (US)

(72) Inventor: Michael Donnenberg, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/974,825

(22) Filed: Aug. 23, 2013

(65) Prior Publication Data

US 2013/0337003 A1    Dec. 19, 2013

Related U.S. Application Data

(63) Continuation of application No. 13/321,399, filed as application No. PCT/US2010/035664 on May 20, 2010, now Pat. No. 8,518,415.

(60) Provisional application No. 61/179,747, filed on May 20, 2009.

(51) Int. Cl.
| | |
|---|---|
| *G01N 33/68* | (2006.01) |
| *A61K 39/08* | (2006.01) |
| *C07K 14/33* | (2006.01) |
| *C07K 16/12* | (2006.01) |

(52) U.S. Cl.
CPC ............ *G01N 33/6893* (2013.01); *A61K 39/08* (2013.01); *C07K 14/33* (2013.01); *C07K 16/1282* (2013.01); *G01N 33/6854* (2013.01)

(58) Field of Classification Search
None
See application file for complete search history.

(56) References Cited

U.S. PATENT DOCUMENTS

| | | | |
|---|---|---|---|
| 6,248,329 B1 * | 6/2001 | Chandrashekar et al. | 424/191.1 |
| 6,290,960 B1 | 9/2001 | Kink | |
| 8,518,415 B2 | 8/2013 | Donnenberg | |
| 2004/0101531 A1 | 5/2004 | Curtiss, III | |
| 2014/0227314 A1 | 8/2014 | Donnenberg | |

FOREIGN PATENT DOCUMENTS

| | | |
|---|---|---|
| WO | 2002/085295 | 10/2002 |
| WO | 2004/099250 | 11/2004 |
| WO | 2007/026247 | 3/2007 |
| WO | 2008/127296 | 10/2008 |
| WO | WO 2008/127296 | * 10/2008 |

OTHER PUBLICATIONS

DuPont et al. Current Opinion in Infectious Diseases 2008, 21:500-507.*
Uniprot Accession #Q181B2 Jul. 25, 2006.*
Proft et al., Pili in Gram-negative and Gram-positive bacteria-structure, assembly and their role in disease, Cell. Mol. Life Sci., 66: 613-635 (2008).
Varga et al., Type IV pili-dependent gliding motility in the Gram-positive pathogen Clostridium perfringens and other Clostridia, Molecular Microbiology, 62: 680-694 (2006).
Dupont et al., New advances in Clostridium difficile infection: changing epidemiology, diagnosis, treatment and control, Current Opinion in Infectious Disease, 21: 500-507 (2008).
Uniprot Accession No. Q180D8. Uniprot Database sequence added Jul. 25, 2006.
Office Action from U.S. Appl. No. 13/321,399, mailed Oct. 25, 2012.
Office Action from U.S. Appl. No. 13/321,399, mailed Aug. 28, 2012.
Van Dissel et al., Bovine antibody-enriched whey to aid in the prevention of a relapse of Clostridium difficile-associated diarrhoea, Journal of Medical Microbiology, 54(2):197-205 (2005).
Torres et al., Evaluation of formalin-inactivated Costridium difficile vaccines administered by parental and mucosal routes of immunization in hamsters, Infection and Immunity, 63(12): 4619-4627 (1995).
UniProt Accession No. Q181B2 Uniprot Database sequence added Jul. 25, 2006.
UniProt Accession No. Q185H8. Uniprot Database sequence added Jul. 25, 2006.
Craig et al., Type IV pili: paradoxes in form and function, Current Opinion in Structural Biology, 18(2):267-277 (Apr. 2008).
Gerd Döring et al., Vaccines and immunotherapy against Pseudomonas aeruginosa, Vaccine, 26(8):1011-1024 (Feb. 2008).
Telford et al., Pili in gram positive pathogens, Nature Reviews Microbiology, 4(7):509-519 (2006).
Office Action from U.S. Appl. No. 14/259,413, mailed May 29, 2014.
Office Action from U.S. Appl. No. 14/259,413, mailed Oct. 8, 2014.
Office Action from U.S. Appl. No. 14/259,413, mailed May 4, 2015.

* cited by examiner

*Primary Examiner* — Oluwatosin Ogunbiyi

(74) *Attorney, Agent, or Firm* — Nevrivy Patent Law Group P.L.L.C.

(57) ABSTRACT

The present invention relates to engineered *Clostridium difficile* type IV pilin (tfp) genes, type IV pilin proteins which can serve as a diagnostic marker for identification of patients infected with *C. difficile*, and vaccines comprising type IV pilin proteins, antigenic fragments and variants thereof for therapeutic interventions.

12 Claims, 3 Drawing Sheets

SEQUENCE LISTING

<160> NUMBER OF SEQ ID NOS: 44

<210> SEQ ID NO 1
<211> LENGTH: 522
<212> TYPE: DNA
<213> ORGANISM: Clostridium difficile

<400> SEQUENCE: 1

```
atgaagttaa aaagaataa aaaaggtttc actttagtgg aattattggt agtaattgca      60
attataggta tattagcagt agtggcagtt ccagctttat ttagtaatat aaacaaggct    120
aaggtagcaa gtgttgagtc tgattatagt tcaattaaga gtgcagcatt atcttattat    180
tcagatacta ataaaatacc agttacacca gatggtcaaa ctggtttaaa tgttttagag    240
acttatatgg aatctcttcc tgataaagct gatataggtg gagaatataa attgattaaa    300
gttggtaata aattagtatt acagataggt aaagatggtg aaggagttac cttaacagaa    360
gcgcaatcag caaaattatt gagtgatata ggtaaagata aatatatac aggtgttaca    420 ggagataatt ttggagagca attaaaagat actacaaaaa tagataataa agctctatat    480
atagtactta tagataatac tgtgatggat tcaacaaaat ag                        522
```

<210> SEQ ID NO 2
<211> LENGTH: 173
<212> TYPE: PRT
<213> ORGANISM: Clostridium difficile

<400> SEQUENCE: 2

```
Met Lys Leu Lys Lys Asn Lys Lys Gly Phe Thr Leu Val Glu Leu Leu
1               5                   10                  15

Val Val Ile Ala Ile Ile Gly Ile Leu Ala Val Ala Val Pro Ala
            20                  25                  30

Leu Phe Ser Asn Ile Asn Lys Ala Lys Val Ala Ser Val Glu Ser Asp
        35                  40                  45

Tyr Ser Ser Ile Lys Ser Ala Ala Leu Ser Tyr Tyr Ser Asp Thr Asn
    50                  55                  60

Lys Ile Pro Val Thr Pro Asp Gly Gln Thr Gly Leu Asn Val Leu Glu
65                  70                  75                  80

Thr Tyr Met Glu Ser Leu Pro Asp Lys Ala Asp Ile Gly Gly Glu Tyr
                85                  90                  95

Lys Leu Ile Lys Val Gly Asn Lys Leu Val Leu Gln Ile Gly Lys Asp
            100                 105                 110

Gly Glu Gly Val Thr Leu Thr Glu Ala Gln Ser Ala Lys Leu Leu Ser
        115                 120                 125

Asp Ile Gly Lys Asp Lys Ile Tyr Thr Gly Val Thr Gly Asp Asn Phe
    130                 135                 140

Gly Glu Gln Leu Lys Asp Thr Thr Lys Ile Asp Asn Lys Ala Leu Tyr
145                 150                 155                 160

Ile Val Leu Ile Asp Asn Thr Val Met Asp Ser Thr Lys
                165                 170
```

<210> SEQ ID NO 3
<211> LENGTH: 558
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
atgcaccatc atcatcatca ttcttctggt ctggtgccac gcggttctgg tatgaaagaa      60
accgctgctg ctaaattcga acgccagcac atggacagcc agatctgggt accgacgac     120 gacgacaagg ccatgggttc taacatcaac aaagctaaag ttgcttctgt tgaatctgac     180
tactcttcta tcaaatctgc tgctctgtct tactactctg acaccaacaa aatcccggtt     240
accccggacg gtcagaccgg tctgaacgtt ctggaaacct acatggaatc tctgccggac     300
aaagctgaca tcggtggtga atacaaactg atcaaagttg gtaacaaact ggttctgcag     360
atcggtaaag acggtgaagg tgttaccctg accgaagctc agtctgctaa actgctgtct     420
gacatcggta agacaaaat ctacaccggt gttaccggtg acaacttcgg tgaacagctg     480
aaagacacca ccaaaatcga caacaaagct ctgtacatcg ttctgatcga caacaccgtt     540
atggactcta ccaaatag                                                  558
```

<210> SEQ ID NO 4
<211> LENGTH: 185
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Ala Met Gly Ser Asn
        35                  40                  45

Ile Asn Lys Ala Lys Val Ala Ser Val Glu Ser Asp Tyr Ser Ser Ile
50                  55                  60

Lys Ser Ala Ala Leu Ser Tyr Tyr Ser Asp Thr Asn Lys Ile Pro Val
65                  70                  75                  80

Thr Pro Asp Gly Gln Thr Gly Leu Asn Val Leu Glu Thr Tyr Met Glu
                85                  90                  95

Ser Leu Pro Asp Lys Ala Asp Ile Gly Gly Glu Tyr Lys Leu Ile Lys
            100                 105                 110

Val Gly Asn Lys Leu Val Leu Gln Ile Gly Lys Asp Gly Glu Gly Val
        115                 120                 125

Thr Leu Thr Glu Ala Gln Ser Ala Lys Leu Leu Ser Asp Ile Gly Lys
    130                 135                 140

Asp Lys Ile Tyr Thr Gly Val Thr Gly Asp Asn Phe Gly Glu Gln Leu
145                 150                 155                 160

Lys Asp Thr Thr Lys Ile Asp Asn Lys Ala Leu Tyr Ile Val Leu Ile
                165                 170                 175

Asp Asn Thr Val Met Asp Ser Thr Lys
            180                 185

<210> SEQ ID NO 5
<211> LENGTH: 522
<212> TYPE: DNA
<213> ORGANISM: Clostridium difficile

<400> SEQUENCE: 5

```
atgaagttaa aaagaataa aaaaggtttc actttagtgg aattattggt agtaattgca      60
attataggta tattagcagt agtggcagtt ccagctttat ttagtaatat aaacaaggct     120
```

```
aaggtagcaa gtgttgagtc tgattatagt tcagttaaga gtgctgcatt atcttattat    180
tcagatacta ataagatacc agttacacca gatggtcaaa ctggtttaag tgttttagaa    240
acttatatgg agtctcttcc tgataaagct gatataggtg agaatataa attgattaaa     300 gttggtagta aattggtatt acagataggt acaaatactg agggagttac cttaacagaa    360
gcacaatcag caaaattatt gagtgatata ggtgaaaaaa aaatatatac aagcgctaca    420
acaaatagtt tgggagatcc attaacaagt aatacaaaaa tagataataa agttctatat    480
atagtactta tagataatac tgtgatggac acaacaaaat ag                       522
```

```
<210> SEQ ID NO 6
<211> LENGTH: 173
<212> TYPE: PRT
<213> ORGANISM: Clostridium difficile

<400> SEQUENCE: 6

Met Lys Leu Lys Lys Asn Lys Lys Gly Phe Thr Leu Val Glu Leu Leu
1               5                   10                  15

Val Val Ile Ala Ile Ile Gly Ile Leu Ala Val Val Ala Val Pro Ala
                20                  25                  30

Leu Phe Ser Asn Ile Asn Lys Ala Lys Val Ala Ser Val Glu Ser Asp
            35                  40                  45

Tyr Ser Ser Val Lys Ser Ala Ala Leu Ser Tyr Tyr Ser Asp Thr Asn
        50                  55                  60

Lys Ile Pro Val Thr Pro Asp Gly Gln Thr Gly Leu Ser Val Leu Glu
65                  70                  75                  80

Thr Tyr Met Glu Ser Leu Pro Asp Lys Ala Asp Ile Gly Gly Glu Tyr
                85                  90                  95

Lys Leu Ile Lys Val Gly Ser Lys Leu Val Leu Gln Ile Gly Thr Asn
            100                 105                 110

Thr Glu Gly Val Thr Leu Thr Glu Ala Gln Ser Ala Lys Leu Leu Ser
        115                 120                 125

Asp Ile Gly Glu Lys Lys Ile Tyr Thr Ser Ala Thr Thr Asn Ser Leu
    130                 135                 140

Gly Asp Pro Leu Thr Ser Asn Thr Lys Ile Asp Asn Lys Val Leu Tyr
145                 150                 155                 160

Ile Val Leu Ile Asp Asn Thr Val Met Asp Thr Thr Lys
                165                 170
```

```
<210> SEQ ID NO 7
<211> LENGTH: 558
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
atgcaccatc atcatcatca ttcttctggt ctggtgccac gcggttctgg tatgaaagaa    60
accgctgctg ctaaattcga acgccagcac atggacagcc cagatctggg taccgacgac    120
gacgacaagg ccatgggttc taacatcaac aaagctaaag ttgcttctgt tgaatctgac    180
tactcttctg ttaaatctgc tgctctgtct tactactctg acaccaacaa aatcccggtt    240
accccggacg gtcagaccgg tctgtctgtt ctggaaacct acatggaatc tctgccggac    300
aaagctgaca tcggtggtga atacaaactg atcaaagttg gttctaaact ggttctgcag    360
```

```
atcggtacca acaccgaagg tgttaccctg accgaagctc agtctgctaa actgctgtct    420
gacatcggtg aaaaaaaaat ctacacctct gctaccacca actctctggg tgacccgctg    480
acctctaaca ccaaaatcga caacaaagtt ctgtacatcg ttctgatcga acaccgtt     540 atggacacca ccaaatag                                                  558
```

<210> SEQ ID NO 8
<211> LENGTH: 185
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

```
Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Ala Met Gly Ser Asn
        35                  40                  45

Ile Asn Lys Ala Lys Val Ala Ser Val Glu Ser Asp Tyr Ser Ser Val
    50                  55                  60

Lys Ser Ala Ala Leu Ser Tyr Tyr Ser Asp Thr Asn Lys Ile Pro Val
65                  70                  75                  80

Thr Pro Asp Gly Gln Thr Gly Leu Ser Val Leu Glu Thr Tyr Met Glu
                85                  90                  95

Ser Leu Pro Asp Lys Ala Asp Ile Gly Gly Glu Tyr Lys Leu Ile Lys
            100                 105                 110

Val Gly Ser Lys Leu Val Leu Gln Ile Gly Thr Asn Thr Glu Gly Val
        115                 120                 125

Thr Leu Thr Glu Ala Gln Ser Ala Lys Leu Leu Ser Asp Ile Gly Glu
    130                 135                 140

Lys Lys Ile Tyr Thr Ser Ala Thr Thr Asn Ser Leu Gly Asp Pro Leu
145                 150                 155                 160

Thr Ser Asn Thr Lys Ile Asp Asn Lys Val Leu Tyr Ile Val Leu Ile
                165                 170                 175

Asp Asn Thr Val Met Asp Thr Thr Lys
            180                 185
```

<210> SEQ ID NO 9
<211> LENGTH: 522
<212> TYPE: DNA
<213> ORGANISM: Clostridium difficile

<400> SEQUENCE: 9

```
atgaagttaa aaagaataa aaaggtttc actttagtgg aattattggt agtaattgca    60
attataggta tattagcagt agtggcagtt ccagctttat ttagtaatat aaacaaggct   120
aaggtagcaa gtgttgagtc tgattatagt tcaattaaga gtgcagcatt atcttattat   180
tcagatacta taaaatacc agttacacca gatggtcaaa ctggtttaaa tgttttagag   240
acttatatgg aatctcttcc tgataaagct gatataggtg gagaatataa attgattaaa   300
gttggtaata aattagtatt acagataggt aaagatggtg aaggagttac cttaacagaa   360
gcgcaatcag caaaattatt gagtgatata ggtaaagata aaatatatac aggtgttaca   420
ggagataatt ttggagagca attaaaagat actacaaaaa tagataataa agctctatat   480
```
atagtactta tagataatac tgtgatggat tcaacaaaat ag					522

<210> SEQ ID NO 10
<211> LENGTH: 173
<212> TYPE: PRT
<213> ORGANISM: Clostridium difficile

<400> SEQUENCE: 10

```
Met Lys Leu Lys Lys Asn Lys Lys Gly Phe Thr Leu Val Glu Leu Leu
1               5                   10                  15

Val Val Ile Ala Ile Ile Gly Ile Leu Ala Val Val Ala Val Pro Ala
            20                  25                  30

Leu Phe Ser Asn Ile Asn Lys Ala Lys Val Ala Ser Val Glu Ser Asp
        35                  40                  45

Tyr Ser Ser Ile Lys Ser Ala Ala Leu Ser Tyr Tyr Ser Asp Thr Asn
    50                  55                  60

Lys Ile Pro Val Thr Pro Asp Gly Gln Thr Gly Leu Asn Val Leu Glu
65                  70                  75                  80

Thr Tyr Met Glu Ser Leu Pro Asp Lys Ala Asp Ile Gly Gly Glu Tyr
                85                  90                  95

Lys Leu Ile Lys Val Gly Asn Lys Leu Val Leu Gln Ile Gly Lys Asp
            100                 105                 110

Gly Glu Gly Val Thr Leu Thr Glu Ala Gln Ser Ala Lys Leu Leu Ser
        115                 120                 125

Asp Ile Gly Lys Asp Lys Ile Tyr Thr Gly Val Thr Gly Asp Asn Phe
    130                 135                 140

Gly Glu Gln Leu Lys Asp Thr Thr Lys Ile Asp Asn Lys Ala Leu Tyr
145                 150                 155                 160

Ile Val Leu Ile Asp Asn Thr Val Met Asp Ser Thr Lys
                165                 170
```

<210> SEQ ID NO 11
<211> LENGTH: 558
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
atgcaccatc atcatcatca ttcttctggt ctggtgccac gcggttctgg tatgaaagaa					60 accgctgctg ctaaattcga acgccagcac atggacagcc agatctgggt accgacgac					120 gacgacaagg ccatgggttc taacatcaac aaagctaaag ttgcttctgt tgaatctgac					180 tactcttcta tcaaatctgc tgctctgtct tactactctg acaccaacaa atcccggtt					240 accccggacg gtcagaccgg tctgaacgtt ctggaaacct acatggaatc tctgccggac					300 aaagctgaca tcggtggtga atacaaactg atcaaagttg gtaacaaact ggttctgcag					360 atcggtaaag acggtgaagg tgttaccctg accgaagctc agtctgctaa actgctgtct					420 gacatcggta agacaaaat ctacaccggt gttaccggtg acaacttcgg tgaacagctg					480 aaagacacca ccaaaatcga caacaaagct ctgtacatcg ttctgatcga caacaccgtt					540 atggactcta ccaaatag					558

<210> SEQ ID NO 12
<211> LENGTH: 185
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met His His His His His Ser Ser Gly Leu Val Pro Arg Gly Ser
1               5                   10                  15

Gly Met Lys Glu Thr Ala Ala Lys Phe Glu Arg Gln His Met Asp
                20                  25                  30

Ser Pro Asp Leu Gly Thr Asp Asp Asp Lys Ala Met Gly Ser Asn
            35                  40                  45

Ile Asn Lys Ala Lys Val Ala Ser Val Glu Ser Asp Tyr Ser Ile
50                  55                  60

Lys Ser Ala Ala Leu Ser Tyr Tyr Ser Asp Thr Asn Lys Ile Pro Val
65                  70                  75                  80

Thr Pro Asp Gly Gln Thr Gly Leu Asn Val Leu Glu Thr Tyr Met Glu
                85                  90                  95

Ser Leu Pro Asp Lys Ala Asp Ile Gly Gly Tyr Lys Leu Ile Lys
            100                 105                 110

Val Gly Asn Lys Leu Val Leu Gln Ile Gly Lys Asp Gly Glu Gly Val
        115                 120                 125

Thr Leu Thr Glu Ala Gln Ser Ala Lys Leu Leu Ser Asp Ile Gly Lys
130                 135                 140

Asp Lys Ile Tyr Thr Gly Val Thr Gly Asp Asn Phe Gly Glu Gln Leu
145                 150                 155                 160

Lys Asp Thr Thr Lys Ile Asp Asn Lys Ala Leu Tyr Ile Val Leu Ile
                165                 170                 175

Asp Asn Thr Val Met Asp Ser Thr Lys
            180                 185

<210> SEQ ID NO 13
<211> LENGTH: 516
<212> TYPE: DNA
<213> ORGANISM: Clostridium difficile

<400> SEQUENCE: 13
atgaagttaa aaagaataa aaaaggtttc actttagtgg aattattggt agtaattgca      60
attataggta tattagcagt agtggcagtt ccagctttat ttagtaatat aaacaaggct    120
aaggtagcaa gtgttgagtc tgattatagt tcagttaaga gtgcagcatt atcttattat    180
tcagatacta ataagatacc agttacacca gatggtcaaa ctggtttaag tgttttagag    240
acttatatgg agtctctgcc tgataaagct gatataggtg gaaatataa attgattaaa    300 gttggtaata aattggtatt acagataggt acaaatactg aaggagttac cttaacagaa    360
gcacaatcag caaaattatt gagtgatata ggtgaaaata aatatatac aaatgcagct    420 cttagtgcta aattaacatc tactacaaag gtaaataatg aagctttata tatagttctt    480
atagataata ttgtaatgga tcaacaagga gcttaa                               516

<210> SEQ ID NO 14
<211> LENGTH: 171
<212> TYPE: PRT
<213> ORGANISM: Clostridium difficile

<400> SEQUENCE: 14

Met Lys Leu Lys Lys Asn Lys Lys Gly Phe Thr Leu Val Glu Leu Leu
1               5                   10                  15

```
Val Val Ile Ala Ile Ile Gly Ile Leu Ala Val Ala Val Pro Ala
            20                  25                  30

Leu Phe Ser Asn Ile Asn Lys Ala Lys Val Ala Ser Val Glu Ser Asp
        35                  40                  45

Tyr Ser Ser Val Lys Ser Ala Ala Leu Ser Tyr Tyr Ser Asp Thr Asn
    50                  55                  60

Lys Ile Pro Val Thr Pro Asp Gly Gln Thr Gly Leu Ser Val Leu Glu
65                  70                  75                  80

Thr Tyr Met Glu Ser Leu Pro Asp Lys Ala Asp Ile Gly Gly Lys Tyr
                85                  90                  95

Lys Leu Ile Lys Val Gly Asn Lys Leu Val Leu Gln Ile Gly Thr Asn
            100                 105                 110

Thr Glu Gly Val Thr Leu Thr Glu Ala Gln Ser Ala Lys Leu Leu Ser
        115                 120                 125

Asp Ile Gly Glu Asn Lys Ile Tyr Thr Asn Ala Ala Leu Ser Ala Lys
    130                 135                 140

Leu Thr Ser Thr Thr Lys Val Asn Asn Glu Ala Leu Tyr Ile Val Leu
145                 150                 155                 160

Ile Asp Asn Ile Val Met Asp Gln Gln Gly Ala
                165                 170

<210> SEQ ID NO 15
<211> LENGTH: 552
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
atgcaccatc atcatcatca ttcttctggt ctggtgccac gcggttctgg tatgaaagaa      60
accgctgctg ctaaattcga acgccagcac atggacagcc agatctgggt accgacgac     120 gacgacaagg ccatgggttc taacatcaac aaagctaaag ttgcttctgt tgaatctgac    180
tactcttctg ttaaatctgc tgctctgtct tactactctg acaccaacaa aatcccggtt    240
accccggacg gtcagaccgg tctgtctgtt ctggaaacct acatggaatc tctgccggac    300
aaagctgaca tcggtggtaa atacaaactg atcaaagttg gtaacaaact ggttctgcag    360
atcggtacca caccgaaggt gttaccctg accgaagctc agtctgctaa actgctgtct    420
gacatcggtg aaaacaaaat ctacaccaac gctgctctgt ctgctaaact gacctctacc    480
accaaagtta caacgaagc tctgtacatc gttctgatcg acaacatcgt tatggaccag    540
cagggtgctt aa                                                        552

<210> SEQ ID NO 16
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Asp Lys Ala Met Gly Ser Asn
```

```
                35                  40                  45
Ile Asn Lys Ala Lys Val Ala Ser Val Glu Ser Asp Tyr Ser Ser Val
     50                  55                  60

Lys Ser Ala Ala Leu Ser Tyr Tyr Ser Asp Thr Asn Lys Ile Pro Val
 65                  70                  75                  80

Thr Pro Asp Gly Gln Thr Gly Leu Ser Val Leu Glu Thr Tyr Met Glu
                 85                  90                  95

Ser Leu Pro Asp Lys Ala Asp Ile Gly Gly Lys Tyr Lys Leu Ile Lys
            100                 105                 110

Val Gly Asn Lys Leu Val Leu Gln Ile Gly Thr Asn Thr Glu Gly Val
        115                 120                 125

Thr Leu Thr Glu Ala Gln Ser Ala Lys Leu Leu Ser Asp Ile Gly Glu
    130                 135                 140

Asn Lys Ile Tyr Thr Asn Ala Ala Leu Ser Ala Lys Leu Thr Ser Thr
145                 150                 155                 160

Thr Lys Val Asn Asn Glu Ala Leu Tyr Ile Val Leu Ile Asp Asn Ile
                165                 170                 175

Val Met Asp Gln Gln Gly Ala
            180

<210> SEQ ID NO 17
<211> LENGTH: 513
<212> TYPE: DNA
<213> ORGANISM: Clostridium difficile

<400> SEQUENCE: 17
atgaagttaa agaagaataa aaaaggtttc actttagtgg aattattggt agtaattgca    60
attataggta tattagcagt agtggcagtt ccagctttat ttagtaatat aaataaggct   120
aaggtagcaa gtgttgagtc tgattatagt tcaattaaga gtgcagcatt atcttattat   180
tcagatacta ataagatgcc agctacaaca tcaaatcctg tagatttaga aaatttaaaa   240
acttatatgg aaagtcttcc tgataaagca gatataggtg gagagtatca attacttttg   300
gttgggaata gttagttttt acaaataaat gatgctacat taacaggagc gcaatcaacg   360
aagttattga gtgatttagg taatgataag atataaaaa ctataggtag cgatgataag   420
cttacagatt tattaactac caatgaaaaa ttagataata aggttctata tttagttctt   480
atagataatg ctgagatgga ttcaacaaaa taa                                513

<210> SEQ ID NO 18
<211> LENGTH: 170
<212> TYPE: PRT
<213> ORGANISM: Clostridium difficile

<400> SEQUENCE: 18

Met Lys Leu Lys Lys Asn Lys Lys Gly Phe Thr Leu Val Glu Leu Leu
  1               5                  10                  15

Val Val Ile Ala Ile Gly Ile Leu Ala Val Val Ala Val Pro Ala
             20                  25                  30

Leu Phe Ser Asn Ile Asn Lys Ala Lys Val Ala Ser Val Glu Ser Asp
         35                  40                  45

Tyr Ser Ser Ile Lys Ser Ala Ala Leu Ser Tyr Tyr Ser Asp Thr Asn
     50                  55                  60

Lys Met Pro Ala Thr Thr Ser Asn Pro Val Asp Leu Glu Asn Leu Lys
 65                  70                  75                  80

Thr Tyr Met Glu Ser Leu Pro Asp Lys Ala Asp Ile Gly Gly Glu Tyr
```

```
                        85                  90                  95
Gln Leu Leu Leu Val Gly Asn Lys Leu Val Leu Gln Ile Asn Asp Ala
                100                 105                 110

Thr Leu Thr Gly Ala Gln Ser Thr Lys Leu Leu Ser Asp Leu Gly Asn
            115                 120                 125

Asp Lys Ile Tyr Lys Thr Ile Gly Ser Asp Asp Lys Leu Thr Asp Leu
        130                 135                 140

Leu Thr Thr Asn Glu Lys Leu Asp Asn Lys Val Leu Tyr Leu Val Leu
145                 150                 155                 160

Ile Asp Asn Ala Glu Met Asp Ser Thr Lys
                165                 170

<210> SEQ ID NO 19
<211> LENGTH: 549
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
atgcaccatc atcatcatca ttcttctggt ctggtgccac gcggttctgg tatgaaagaa    60
accgctgctg ctaaattcga acgccagcac atggacagcc agatctggg taccgacgac    120 gacgacaagg ccatgggttc taacatcaac aaagctaaag ttgcttctgt tgaatctgac    180
tactcttcta tcaaatctgc tgctctgtct tactactctg acaccaacaa aatgccggct    240
accacctcta acccggttga cctggaaaac ctgaaaacct acatggaatc tctgccggac    300
aaagctgaca tcggtggtga ataccagctg ctgctggttg gtaacaaact ggttctgcag    360
atcaacgacg ctaccctgac cggtgctcag tctaccaaac tgctgtctga cctgggtaac    420
gacaaaatct acaaaaccat cggttctgac gacaaactga ccgacctgct gaccaccaac    480
gaaaaactgg acaacaaagt tctgtacctg gttctgatcg acaacgctga atggactct    540 accaaataa                                                            549

<210> SEQ ID NO 20
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met His His His His His Ser Ser Gly Leu Val Pro Arg Gly Ser
1               5                   10                  15

Gly Met Lys Glu Thr Ala Ala Ala Lys Phe Glu Arg Gln His Met Asp
                20                  25                  30

Ser Pro Asp Leu Gly Thr Asp Asp Asp Asp Lys Ala Met Gly Ser Asn
            35                  40                  45

Ile Asn Lys Ala Lys Val Ala Ser Val Glu Ser Asp Tyr Ser Ser Ile
        50                  55                  60

Lys Ser Ala Ala Leu Ser Tyr Tyr Ser Asp Thr Asn Lys Met Pro Ala
65                  70                  75                  80

Thr Thr Ser Asn Pro Val Asp Leu Glu Asn Leu Lys Thr Tyr Met Glu
                85                  90                  95

Ser Leu Pro Asp Lys Ala Asp Ile Gly Gly Glu Tyr Gln Leu Leu Leu
                100                 105                 110
```

```
Val Gly Asn Lys Leu Val Leu Gln Ile Asn Asp Ala Thr Leu Thr Gly
        115                 120                 125

Ala Gln Ser Thr Lys Leu Leu Ser Asp Leu Gly Asn Asp Lys Ile Tyr
130                 135                 140

Lys Thr Ile Gly Ser Asp Asp Lys Leu Thr Leu Leu Thr Thr Asn
145                 150                 155                 160

Glu Lys Leu Asp Asn Lys Val Leu Tyr Leu Val Leu Ile Asp Asn Ala
                165                 170                 175

Glu Met Asp Ser Thr Lys
            180
```

<210> SEQ ID NO 21
<211> LENGTH: 360
<212> TYPE: DNA
<213> ORGANISM: Clostridium difficile

<400> SEQUENCE: 21

```
ttgataaatt tgataaataa aaaacgaaaa ggatttacac ttgttgaaat gattgtagta      60
gtaactattt taggcgttat atctagtata gcattagtta agtatagtaa ggttcaagaa     120
agtgccaaat taaatgcaga ctatacgaat gctgctaata tagtaactgc agctagcatg     180
gcaattaatg atgatgaaaa gacaatagac tctctaagtg tagaaacatt gaaggaaaag     240
ggatacctaa atactgttcc agttcctcag agtacatcag gtaaattcga acttgtcata     300
aatgatagcg aacagatat aagcgtaaat ataaattcta aacaatttta tccaaaataa      360
```

<210> SEQ ID NO 22
<211> LENGTH: 119
<212> TYPE: PRT
<213> ORGANISM: Clostridium difficile

<400> SEQUENCE: 22

```
Met Ile Asn Leu Ile Asn Lys Lys Arg Lys Gly Phe Thr Leu Val Glu
1               5                   10                  15

Met Ile Val Val Val Thr Ile Leu Gly Val Ile Ser Ser Ile Ala Leu
                20                  25                  30

Val Lys Tyr Ser Lys Val Gln Glu Ser Ala Lys Leu Asn Ala Asp Tyr
            35                  40                  45

Thr Asn Ala Ala Asn Ile Val Thr Ala Ala Ser Met Ala Ile Asn Asp
        50                  55                  60

Asp Glu Lys Thr Ile Asp Ser Leu Ser Val Glu Thr Leu Lys Glu Lys
65                  70                  75                  80

Gly Tyr Leu Asn Thr Val Pro Val Pro Gln Ser Thr Ser Gly Lys Phe
                85                  90                  95

Glu Leu Val Ile Asn Asp Ser Gly Thr Asp Ile Ser Val Asn Ile Asn
            100                 105                 110

Ser Lys Gln Phe Tyr Pro Lys
        115
```

<210> SEQ ID NO 23
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
atgcaccatc atcatcatca ttcttctggt ctggtgccac gcggttctgg tatgaaagaa    60
accgctgctg ctaaattcga acgccagcac atggacagcc agatctggg taccgacgac    120 gacgacaagg ccatgggtaa atactctaaa gttcaggaat ctgctaaact gaacgctgac    180
tacaccaacg ctgctaacat cgttaccgct gcttctatgg ctatcaacga cgacgaaaaa    240
accatcgact ctctgtctgt tgaaaccctg aaagaaaaag gttacctgaa caccgttccg    300
gttccgcagt ctacctctgg taaattcgaa ctggttatca acgactctgg taccgacatc    360
tctgttaaca tcaactctaa acagttctac ccgaaataa                          399
```

<210> SEQ ID NO 24
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Met His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Ala Met Gly Lys Tyr
        35                  40                  45

Ser Lys Val Gln Glu Ser Ala Lys Leu Asn Ala Asp Tyr Thr Asn Ala
    50                  55                  60

Ala Asn Ile Val Thr Ala Ala Ser Met Ala Ile Asn Asp Asp Glu Lys
65                  70                  75                  80

Thr Ile Asp Ser Leu Ser Val Glu Thr Leu Lys Glu Lys Gly Tyr Leu
                85                  90                  95

Asn Thr Val Pro Val Pro Gln Ser Thr Ser Gly Lys Phe Glu Leu Val
            100                 105                 110

Ile Asn Asp Ser Gly Thr Asp Ile Ser Val Asn Ile Asn Ser Lys Gln
        115                 120                 125

Phe Tyr Pro Lys
    130
```

<210> SEQ ID NO 25
<211> LENGTH: 351
<212> TYPE: DNA
<213> ORGANISM: Clostridium difficile

<400> SEQUENCE: 25

```
ttgataaata aaaacgaaa aggatttaca cttgttgaaa tgattgtagt agtaactatt    60
ttaggagtta tatctagtat agcattagtt aagtatagta aggttcaaga aagtgctaaa   120
ttaaatgcag actatacgaa tgctgctaat atagtaacag cagctagtat ggcaattaat   180
gatgatgaaa atataataga ctctctaagt gtagaagcat tgaaggaaaa gggataccta   240
aatactgttc cagttcctca gagtacatca ggtaaattcg aacttgttat aaatgataac   300
ggaacagata taagcgtgaa tataaattct aagcaatttt atccaaaata a            351
```

<210> SEQ ID NO 26
<211> LENGTH: 116
<212> TYPE: PRT
<213> ORGANISM: Clostridium difficile

<400> SEQUENCE: 26

```
Met Ile Asn Lys Lys Arg Lys Gly Phe Thr Leu Val Glu Met Ile Val
1               5                   10                  15

Val Val Thr Ile Leu Gly Val Ile Ser Ser Ile Ala Leu Val Lys Tyr
            20                  25                  30

Ser Lys Val Gln Glu Ser Ala Lys Leu Asn Ala Asp Tyr Thr Asn Ala
            35                  40                  45

Ala Asn Ile Val Thr Ala Ala Ser Met Ala Ile Asn Asp Asp Glu Asn
        50                  55                  60

Ile Ile Asp Ser Leu Ser Val Glu Ala Leu Lys Glu Lys Gly Tyr Leu
65                  70                  75                  80

Asn Thr Val Pro Val Pro Gln Ser Thr Ser Gly Lys Phe Glu Leu Val
                85                  90                  95

Ile Asn Asp Asn Gly Thr Asp Ile Ser Val Asn Ile Asn Ser Lys Gln
                100                 105                 110

Phe Tyr Pro Lys
        115
```

<210> SEQ ID NO 27
<211> LENGTH: 399
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27

```
atgcaccatc atcatcatca ttcttctggt ctggtgccac gcggttctgg tatgaaagaa      60
accgctgctg ctaaattcga acgccagcac atggacagcc agatctggg taccgacgac      120
gacgacaagg ccatgggtaa atactctaaa gttcaggaat ctgctaaact gaacgctgac    180
tacaccaacg ctgctaacat cgttaccgct gcttctatgg ctatcaacga cgacgaaaac    240
atcatcgact ctctgtctgt tgaagctctg aaagaaaaag gttacctgaa caccgttccg    300
gttccgcagt ctacctctgg taaattcgaa ctggttatca acgacaacgg taccgacatc    360
tctgttaaca tcaactctaa acagttctac ccgaaataa                           399
```

<210> SEQ ID NO 28
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

```
Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Ala Met Gly Lys Tyr
            35                  40                  45

Ser Lys Val Gln Glu Ser Ala Lys Leu Asn Ala Asp Tyr Thr Asn Ala
        50                  55                  60

Ala Asn Ile Val Thr Ala Ala Ser Met Ala Ile Asn Asp Asp Glu Asn
65                  70                  75                  80

Ile Ile Asp Ser Leu Ser Val Glu Ala Leu Lys Glu Lys Gly Tyr Leu
                85                  90                  95
```

```
Asn Thr Val Pro Val Pro Gln Ser Thr Ser Gly Lys Phe Glu Leu Val
            100                 105                 110

Ile Asn Asp Asn Gly Thr Asp Ile Ser Val Asn Ile Asn Ser Lys Gln
        115                 120                 125

Phe Tyr Pro Lys
        130

<210> SEQ ID NO 29
<211> LENGTH: 495
<212> TYPE: DNA
<213> ORGANISM: Clostridium difficile

<400> SEQUENCE: 29
atgaaaaata aaaaggatt tactctagtg gaattattag tagtaattgc tataatagga      60
atattggcaa taatagcact tccagcatta tttaaaaata tagaaaaagc aaagatagct    120
aaacttgaag ctgatataag tgcaataaaa agtgcatctc ttagttacta tgctgatgaa    180
tccaagtata ctgatggagg aatgatatca tgggtaaaga agatggaaa ataataata     240 aatgggggtt ttaaagatga cccattagca gataaaatag aaatttagg gatgccttat    300 aatggttcat atctgttaat gtcatctcct ggtcatgaaa aatatctaga attaagcata   360
cttccagaag gagaaataag caaaagtggt ctagataaat aaaaaatga ttatggaaat    420 ttaatagaca taacgaacga tcaaaataaa ataatattg taataaaact tttaaataat    480
aaatcgaata cttaa                                                     495

<210> SEQ ID NO 30
<211> LENGTH: 164
<212> TYPE: PRT
<213> ORGANISM: Clostridium difficile

<400> SEQUENCE: 30

Met Lys Asn Lys Lys Gly Phe Thr Leu Val Glu Leu Leu Val Val Ile
1               5                   10                  15

Ala Ile Ile Gly Ile Leu Ala Ile Ile Ala Leu Pro Ala Leu Phe Lys
            20                  25                  30

Asn Ile Glu Lys Ala Lys Ile Ala Lys Leu Glu Ala Asp Ile Ser Ala
        35                  40                  45

Ile Lys Ser Ala Ser Leu Ser Tyr Tyr Ala Asp Glu Ser Lys Tyr Thr
    50                  55                  60

Asp Gly Gly Met Ile Ser Trp Val Lys Lys Asp Gly Lys Ile Ile Ile
65                  70                  75                  80

Asn Gly Gly Phe Lys Asp Asp Pro Leu Ala Asp Lys Ile Glu Asn Leu
                85                  90                  95

Gly Met Pro Tyr Asn Gly Ser Tyr Leu Leu Met Ser Ser Pro Gly His
            100                 105                 110

Glu Lys Tyr Leu Glu Leu Ser Ile Leu Pro Glu Gly Glu Ile Ser Lys
        115                 120                 125

Ser Gly Leu Asp Lys Leu Lys Asn Asp Tyr Gly Asn Leu Ile Asp Ile
    130                 135                 140

Thr Asn Asp Gln Asn Lys Ile Asn Ile Val Ile Lys Leu Leu Asn Asn
145                 150                 155                 160

Lys Ser Asn Thr

<210> SEQ ID NO 31
<211> LENGTH: 540
<212> TYPE: DNA
```

<210> SEQ ID NO 31
<211> LENGTH: 540
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 31

```
atgcaccatc atcatcatca ttcttctggt ctggtgccac gcggttctgg tatgaaagaa    60
accgctgctg ctaaattcga acgccagcac atggacagcc agatctggg taccgacgac   120
gacgacaagg ccatgggtaa aaacatcgaa aaagctaaaa tcgctaaact ggaagctgac   180
atctctgcta tcaaatctgc ttctctgtct tactacgctg acgaatctaa atacaccgac   240
ggtggtatga tctcttgggt taaaaaagac ggtaaaatca tcatcaacgg tggtttcaaa   300
gacgacccgc tggctgacaa aatcgaaaac ctgggtatgc cgtacaacgg ttcttacctg   360
ctgatgtctt ctccgggtca cgaaaaatac ctggaactgt ctatcctgcc ggaaggtgaa   420
atctctaaat ctggtctgga caaactgaaa aacgactacg gtaacctgat cgacatcacc   480
aacgaccaga caaaatcaa catcgttatc aaactgctga caacaaatc taacacctaa   540
```

<210> SEQ ID NO 32
<211> LENGTH: 179
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

```
Met His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Asp Lys Ala Met Gly Lys Asn
        35                  40                  45

Ile Glu Lys Ala Lys Ile Ala Lys Leu Glu Ala Asp Ile Ser Ala Ile
    50                  55                  60

Lys Ser Ala Ser Leu Ser Tyr Tyr Ala Asp Glu Ser Lys Tyr Thr Asp
65                  70                  75                  80

Gly Gly Met Ile Ser Trp Val Lys Lys Asp Gly Lys Ile Ile Ile Asn
                85                  90                  95

Gly Gly Phe Lys Asp Asp Pro Leu Ala Asp Lys Ile Glu Asn Leu Gly
            100                 105                 110

Met Pro Tyr Asn Gly Ser Tyr Leu Leu Met Ser Ser Pro Gly His Glu
        115                 120                 125

Lys Tyr Leu Glu Leu Ser Ile Leu Pro Glu Gly Glu Ile Ser Lys Ser
    130                 135                 140

Gly Leu Asp Lys Leu Lys Asn Asp Tyr Gly Asn Leu Ile Asp Ile Thr
145                 150                 155                 160

Asn Asp Gln Asn Lys Ile Asn Ile Val Ile Lys Leu Leu Asn Asn Lys
                165                 170                 175

Ser Asn Thr
```

<210> SEQ ID NO 33
<211> LENGTH: 495
<212> TYPE: DNA
<213> ORGANISM: Clostridium difficile

<400> SEQUENCE: 33

```
atgaaaaata aaaaaggatt tactctagtg gaattattag tagtaattgc tataataqga      60 atattggcaa tagtagcact tccagcatta tttaaaaata tagaaaaagc aaagatagct     120
aaacttgaag ctgatataag tgcaataaaa agtgcgtctc ttagctacta tgcagatgaa     180
tcaaaatata ctgatggagg aatgatatca tgggtaaaga agatggaaa  ataataata     240 aatggtggct ttaaagatga cccattagca gataaaatag aaaatttagg tatgccttat     300
aatggttcat atctattaat gtcatctcct ggtcatgaaa aatatctaga attaagtata     360
cttccagaag gagaaataag caaaagtggt ctagataaat aaaaagtga  ttatggaagt     420 tcaatagaca taaagaacga tcaaaacaaa atagatattg  taataaaact tttaaatgat    480
aaatcgaata cttaa                                                      495
```

<210> SEQ ID NO 34
<211> LENGTH: 164
<212> TYPE: PRT
<213> ORGANISM: Clostridium difficile
<400> SEQUENCE: 34

```
Met Lys Asn Lys Lys Gly Phe Thr Leu Val Glu Leu Leu Val Val Ile
1               5                   10                  15

Ala Ile Ile Gly Ile Leu Ala Ile Val Ala Leu Pro Ala Leu Phe Lys
            20                  25                  30

Asn Ile Glu Lys Ala Lys Ile Ala Lys Leu Glu Ala Asp Ile Ser Ala
        35                  40                  45

Ile Lys Ser Ala Ser Leu Ser Tyr Tyr Ala Asp Glu Ser Lys Tyr Thr
    50                  55                  60

Asp Gly Gly Met Ile Ser Trp Val Lys Lys Asp Gly Lys Ile Ile Ile
65                  70                  75                  80

Asn Gly Gly Phe Lys Asp Asp Pro Leu Ala Asp Lys Ile Glu Asn Leu
                85                  90                  95

Gly Met Pro Tyr Asn Gly Ser Tyr Leu Leu Met Ser Ser Pro Gly His
            100                 105                 110

Glu Lys Tyr Leu Glu Leu Ser Ile Leu Pro Glu Gly Glu Ile Ser Lys
        115                 120                 125

Ser Gly Leu Asp Lys Leu Lys Ser Asp Tyr Gly Ser Ser Ile Asp Ile
    130                 135                 140

Lys Asn Asp Gln Asn Lys Ile Asp Ile Val Ile Lys Leu Leu Asn Asp
145                 150                 155                 160

Lys Ser Asn Thr
```

<210> SEQ ID NO 35
<211> LENGTH: 540
<212> TYPE: DNA
<213> ORGANISM: Artificial Sequence
<220> FEATURE:
<223> OTHER INFORMATION: Description of Artificial Sequence: Synthetic
      polynucleotide <400> SEQUENCE: 35

```
atgcaccatc atcatcatca ttcttctggt ctggtgccac gcggttctgg tatgaaagaa      60
accgctgctg ctaaattcga acgccagcac atggacagcc agatctgggt accgacgac     120 gacgacaagg ccatgggtaa aacatcgaa  aaagctaaaa tcgctaaact ggaagctgac     180
atctctgcta tcaaatctgc ttctctgtct tactacgctg acgaatctaa atacaccgac     240
ggtggtatga tctcttgggt taaaaagac  ggtaaaatca tcatcaacgg tggtttcaaa     300
```

```
gacgacccgc tggctgacaa aatcgaaaac ctgggtatgc cgtacaacgg ttcttacctg      360
ctgatgtctt ctccgggtca cgaaaaatac ctggaactgt ctatcctgcc ggaaggtgaa      420
atctctaaat ctggtctgga caaactgaaa tctgactacg gttcttctat cgacatcaaa      480
aacgaccaga caaaatcga catcgttatc aaactgctga cgacaaatc taacacctaa       540
```

```
<210> SEQ ID NO 36
<211> LENGTH: 179
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36
```

Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Ala Met Gly Lys Asn
        35                  40                  45

Ile Glu Lys Ala Lys Ile Ala Lys Leu Glu Ala Asp Ile Ser Ala Ile
    50                  55                  60

Lys Ser Ala Ser Leu Ser Tyr Tyr Ala Asp Glu Ser Lys Tyr Thr Asp
65                  70                  75                  80

Gly Gly Met Ile Ser Trp Val Lys Asp Gly Lys Ile Ile Ile Asn
                85                  90                  95

Gly Gly Phe Lys Asp Asp Pro Leu Ala Asp Lys Ile Glu Asn Leu Gly
            100                 105                 110

Met Pro Tyr Asn Gly Ser Tyr Leu Leu Met Ser Ser Pro Gly His Glu
        115                 120                 125

Lys Tyr Leu Glu Leu Ser Ile Leu Pro Glu Gly Glu Ile Ser Lys Ser
    130                 135                 140

Gly Leu Asp Lys Leu Lys Ser Asp Tyr Gly Ser Ser Ile Asp Ile Lys
145                 150                 155                 160

Asn Asp Gln Asn Lys Ile Asp Ile Val Ile Lys Leu Leu Asn Asp Lys
                165                 170                 175

Ser Asn Thr

```
<210> SEQ ID NO 37
<211> LENGTH: 489
<212> TYPE: DNA
<213> ORGANISM: Clostridium difficile

<400> SEQUENCE: 37
atgaaaaata aaaaaggatt tactctagtg gaattattag tagtaattgc tataatagga      60
atattggcaa tagtagcact tccagcatta tttaaaaata tagaaaaagc aaagatagct     120
aaacttgaag ctgatataag tgcaataaaa agtgcgtctc ttagctacta tgcagatgaa     180
tcaaaatata ctgaaggaaa cataatatgg tggactaaaa aagatggaaa ataacagta     240 aactctggta ttggtgatga agacccttttg gcacataaaa tagaaaattt aggcatgcct     300
tataatggtt cgtacacttt agtgtcatct aatggtagtg aagaatactt agaattaaac     360
ataattatag atggagaaat aagtaaaagt ggtctagata aattagaaga agattatggt     420
agttcaataa caataccaaa tgataaaaat atgataataa cttttttatc taataaatca     480
gacaattaa                                                             489
```

<210> SEQ ID NO 38
<211> LENGTH: 162
<212> TYPE: PRT
<213> ORGANISM: Clostridium difficile

<400> SEQUENCE: 38

```
Met Lys Asn Lys Lys Gly Phe Thr Leu Val Glu Leu Val Val Ile
1               5                   10                  15

Ala Ile Ile Gly Ile Leu Ala Ile Val Ala Leu Pro Ala Leu Phe Lys
            20                  25                  30

Asn Ile Glu Lys Ala Lys Ile Ala Lys Leu Glu Ala Asp Ile Ser Ala
        35                  40                  45

Ile Lys Ser Ala Ser Leu Ser Tyr Tyr Ala Asp Glu Ser Lys Tyr Thr
    50                  55                  60

Glu Gly Asn Ile Ile Trp Trp Thr Lys Lys Asp Gly Lys Ile Thr Val
65                  70                  75                  80

Asn Ser Gly Ile Gly Asp Glu Asp Pro Leu Ala His Lys Ile Glu Asn
                85                  90                  95

Leu Gly Met Pro Tyr Asn Gly Ser Tyr Thr Leu Val Ser Ser Asn Gly
            100                 105                 110

Ser Glu Glu Tyr Leu Glu Leu Asn Ile Ile Ile Asp Gly Glu Ile Ser
        115                 120                 125

Lys Ser Gly Leu Asp Lys Leu Glu Glu Asp Tyr Gly Ser Ser Ile Thr
    130                 135                 140

Ile Pro Asn Asp Lys Asn Met Ile Ile Thr Phe Leu Ser Asn Lys Ser
145                 150                 155                 160

Asp Asn
```

<210> SEQ ID NO 39
<211> LENGTH: 534
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 39

```
atgcaccatc atcatcatca ttcttctggt ctggtgccac gcggttctgg tatgaaagaa      60
accgctgctg ctaaattcga acgccagcac atggacagcc agatctgggt accgacgac     120
gacgacaagg ccatgggtaa aaacatcgaa aaagctaaaa tcgctaaact ggaagctgac    180
atctctgcta tcaaatctgc ttctctgtct tactacgctg acgaatctaa atacaccgaa    240
ggtaacatca tctggtggac caaaaaagac ggtaaaatca ccgttaactc tggtatcggt    300
gacgaagacc cgctggctca caaaatcgaa aacctgggta tgccgtacaa cggttcttac    360
accctggttt cttctaacgg ttctgaagaa tacctggaac tgaacatcat catcgacggt    420
gaaatctcta atctggtct ggacaaactg gaagaagact acggttcttc tatcaccatc    480
ccgaacgaca aaaacatgat catcaccttc ctgtctaaca atctgacaa ctaa            534
```

<210> SEQ ID NO 40
<211> LENGTH: 177
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

```
Met His His His His His Ser Ser Gly Leu Val Pro Arg Gly Ser
1               5                   10                  15

Gly Met Lys Glu Thr Ala Ala Lys Phe Glu Arg Gln His Met Asp
            20                  25                  30

Ser Pro Asp Leu Gly Thr Asp Asp Asp Lys Ala Met Gly Lys Asn
        35                  40                  45

Ile Glu Lys Ala Lys Ile Ala Lys Leu Glu Ala Asp Ile Ser Ala Ile
    50                  55                  60

Lys Ser Ala Ser Leu Ser Tyr Tyr Ala Asp Glu Ser Lys Tyr Thr Glu
65                  70                  75                  80

Gly Asn Ile Ile Trp Trp Thr Lys Lys Asp Gly Lys Ile Thr Val Asn
                85                  90                  95

Ser Gly Ile Gly Asp Glu Asp Pro Leu Ala His Lys Ile Glu Asn Leu
            100                 105                 110

Gly Met Pro Tyr Asn Gly Ser Tyr Thr Leu Val Ser Ser Asn Gly Ser
            115                 120                 125

Glu Glu Tyr Leu Glu Leu Asn Ile Ile Asp Gly Glu Ile Ser Lys
130                 135                 140

Ser Gly Leu Asp Lys Leu Glu Glu Asp Tyr Gly Ser Ser Ile Thr Ile
145                 150                 155                 160

Pro Asn Asp Lys Asn Met Ile Ile Thr Phe Leu Ser Asn Lys Ser Asp
                165                 170                 175

Asn
```

<210> SEQ ID NO 41
<211> LENGTH: 819
<212> TYPE: DNA
<213> ORGANISM: Clostridium difficile

<400> SEQUENCE: 41

```
atgggaatga ttattatgaa taaaaagggt tttacattaa ttgaattgtt ggtagttata    60
tctataatag gaattttagt tatagtagct gttccagcgt tatttagaaa tatagaaaaa   120
agtaaggcag ttacatgtct ttctaataga gaaaatataa agactcaaat tgttattgca   180
atggctgagg aatcaagtaa agacaagaat gaagtcataa agaggtatt agaaaacaaa    240
gatggtaagt actttgaaac agaaccaaag tgtaagtcag gtggaatata ttcagcaacg   300
tttgatgatg gttatgatgg aataactgga atagaaagca ttgcaaaagt gtatgttact   360
tgtacaaaac atccagatgg tattgaaatg gctaggata tacatcaaag tatgaaagat    420
ttgattgcat catttgcaca agaccttct ataataccag gagcttcaaa gggcaatgat    480
gattttagaa atatttatt agacaataaa tataaaaatg ggtggcctac aattccagat    540
gaatttaagg caaatatgg attaagtaag gatacactat atatacaacc atatgcatat    600
aatcctacta atctgatgc tactgtagtt gtatttgcaa ataataagac tggaggtaat    660
tggtatactt ccctagttta cgattatgat gaaggtagat ggtataaagg taaaaatggt   720
atttctgttg caggtaggtc atgggatgtt gacacagata gtgttaagtc tgtaaaaaca   780
gagattcatt ctaagagggg atggggtcct ttaaattaa                          819
```

<210> SEQ ID NO 42
<211> LENGTH: 272
<212> TYPE: PRT
<213> ORGANISM: Clostridium difficile

<400> SEQUENCE: 42

```
Met Gly Met Ile Ile Met Asn Lys Lys Gly Phe Thr Leu Ile Glu Leu
1               5                   10                  15
Leu Val Val Ile Ser Ile Ile Gly Ile Leu Val Ile Ala Val Pro
            20                  25                  30
Ala Leu Phe Arg Asn Ile Glu Lys Ser Lys Ala Val Thr Cys Leu Ser
        35                  40                  45
Asn Arg Glu Asn Ile Lys Thr Gln Ile Val Ile Ala Met Ala Glu Glu
50                  55                  60
Ser Ser Lys Asp Lys Asn Glu Val Ile Lys Glu Val Leu Glu Asn Lys
65                  70                  75                  80
Asp Gly Lys Tyr Phe Glu Thr Glu Pro Lys Cys Lys Ser Gly Gly Ile
                85                  90                  95
Tyr Ser Ala Thr Phe Asp Gly Tyr Asp Gly Ile Thr Gly Ile Glu
            100                 105                 110
Ser Ile Ala Lys Val Tyr Val Thr Cys Thr Lys His Pro Asp Gly Ile
        115                 120                 125
Glu Met Ala Arg Asp Ile His Gln Ser Met Lys Asp Leu Ile Ala Ser
130                 135                 140
Phe Ala Gln Asp Pro Ser Ile Ile Pro Gly Ala Ser Lys Gly Asn Asp
145                 150                 155                 160
Asp Phe Arg Lys Tyr Leu Leu Asp Asn Lys Tyr Lys Asn Gly Trp Pro
                165                 170                 175
Thr Ile Pro Asp Glu Phe Lys Ala Lys Tyr Gly Leu Ser Lys Asp Thr
            180                 185                 190
Leu Tyr Ile Gln Pro Tyr Ala Tyr Asn Pro Thr Lys Ser Asp Ala Thr
        195                 200                 205
Val Val Val Phe Ala Asn Asn Lys Thr Gly Gly Asn Trp Tyr Thr Ser
210                 215                 220
Leu Val Tyr Asp Tyr Asp Glu Gly Arg Trp Tyr Lys Gly Lys Asn Gly
225                 230                 235                 240
Ile Ser Val Ala Gly Arg Ser Trp Asp Val Asp Thr Asp Ser Val Lys
                245                 250                 255
Ser Val Lys Thr Glu Ile His Ser Lys Glu Gly Trp Gly Pro Leu Asn
            260                 265                 270
```

<210> SEQ ID NO 43
<211> LENGTH: 852
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 43

```
atgcaccatc atcatcatca ttcttctggt ctggtgccac gcggttctgg tatgaaagaa        60
accgctgctg ctaaattcga acgccagcac atggacagcc agatctgggt accgacgac       120
gacgacaagg ccatgggtcg taacatcgaa aaatctaaag ctgttacctg cctgtctaac       180
cgtgaaaaca tcaaaaccca gatcgttatc gctatggctg aagaatcttc taaagacaaa       240
aacgaagtta tcaaagaagt tctggaaaac aaagacggta atacttcga accgaaccg        300
aaatgcaaat ctggtggtat ctactctgct accttcgacg acggttacga cggtatcacc       360
ggtatcgaat ctatcgctaa agtttacgtt acctgccacaa acaccccgga cggtatcgaa       420
atggctcgtg acatccacca gtctatgaaa gacctgatcg cttctttcgc tcaggacccg       480
```

```
tctatcatcc cgggtgcttc taaaggtaac gacgacttcc gtaaatacct gctggacaac    540
aaatacaaaa acggttggcc gaccatcccg gacgaattca aagctaaata cggtctgtct    600
aaagacaccc tgtacatcca gccgtacgct tacaacccga ccaaatctga cgctaccgtt    660
gttgttttcg ctaacaacaa aaccggtggt aactggtaca cctctctggt ttacgactac    720
gacgaaggtc gttggtacaa aggtaaaaac ggtatctctg ttgctggtcg ttcttgggac    780
gttgacaccg actctgttaa atctgttaaa accgaaatcc actctaaaga aggttggggt    840
ccgctgaact aa                                                       852
```

```
<210> SEQ ID NO 44
<211> LENGTH: 283
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Ala Met Gly Arg Asn
        35                  40                  45

Ile Glu Lys Ser Lys Ala Val Thr Cys Leu Ser Asn Arg Glu Asn Ile
    50                  55                  60

Lys Thr Gln Ile Val Ile Ala Met Ala Glu Glu Ser Ser Lys Asp Lys
65                  70                  75                  80

Asn Glu Val Ile Lys Glu Val Leu Glu Asn Lys Asp Gly Lys Tyr Phe
                85                  90                  95

Glu Thr Glu Pro Lys Cys Lys Ser Gly Gly Ile Tyr Ser Ala Thr Phe
            100                 105                 110

Asp Asp Gly Tyr Asp Gly Ile Thr Gly Ile Glu Ser Ile Ala Lys Val
        115                 120                 125

Tyr Val Thr Cys Thr Lys His Pro Asp Gly Ile Glu Met Ala Arg Asp
    130                 135                 140

Ile His Gln Ser Met Lys Asp Leu Ile Ala Ser Phe Ala Gln Asp Pro
145                 150                 155                 160

Ser Ile Ile Pro Gly Ala Ser Lys Gly Asn Asp Asp Phe Arg Lys Tyr
                165                 170                 175

Leu Leu Asp Asn Lys Tyr Lys Asn Gly Trp Pro Thr Ile Pro Asp Glu
            180                 185                 190

Phe Lys Ala Lys Tyr Gly Leu Ser Lys Asp Thr Leu Tyr Ile Gln Pro
        195                 200                 205

Tyr Ala Tyr Asn Pro Thr Lys Ser Asp Ala Thr Val Val Val Phe Ala
    210                 215                 220

Asn Asn Lys Thr Gly Gly Asn Trp Tyr Thr Ser Leu Val Tyr Asp Tyr
225                 230                 235                 240
```

```
Asp Glu Gly Arg Trp Tyr Lys Gly Lys Asn Gly Ile Ser Val Ala Gly
            245                 250                 255

Arg Ser Trp Asp Val Asp Thr Asp Ser Val Lys Ser Val Lys Thr Glu
            260                 265                 270

Ile His Ser Lys Glu Gly Trp Gly Pro Leu Asn
            275                 280
```

ENGINEERED TYPE IV PILIN OF CLOSTRIDIUM DIFFICILE

CROSS REFERENCE TO RELATED APPLICATIONS

Figure 1:
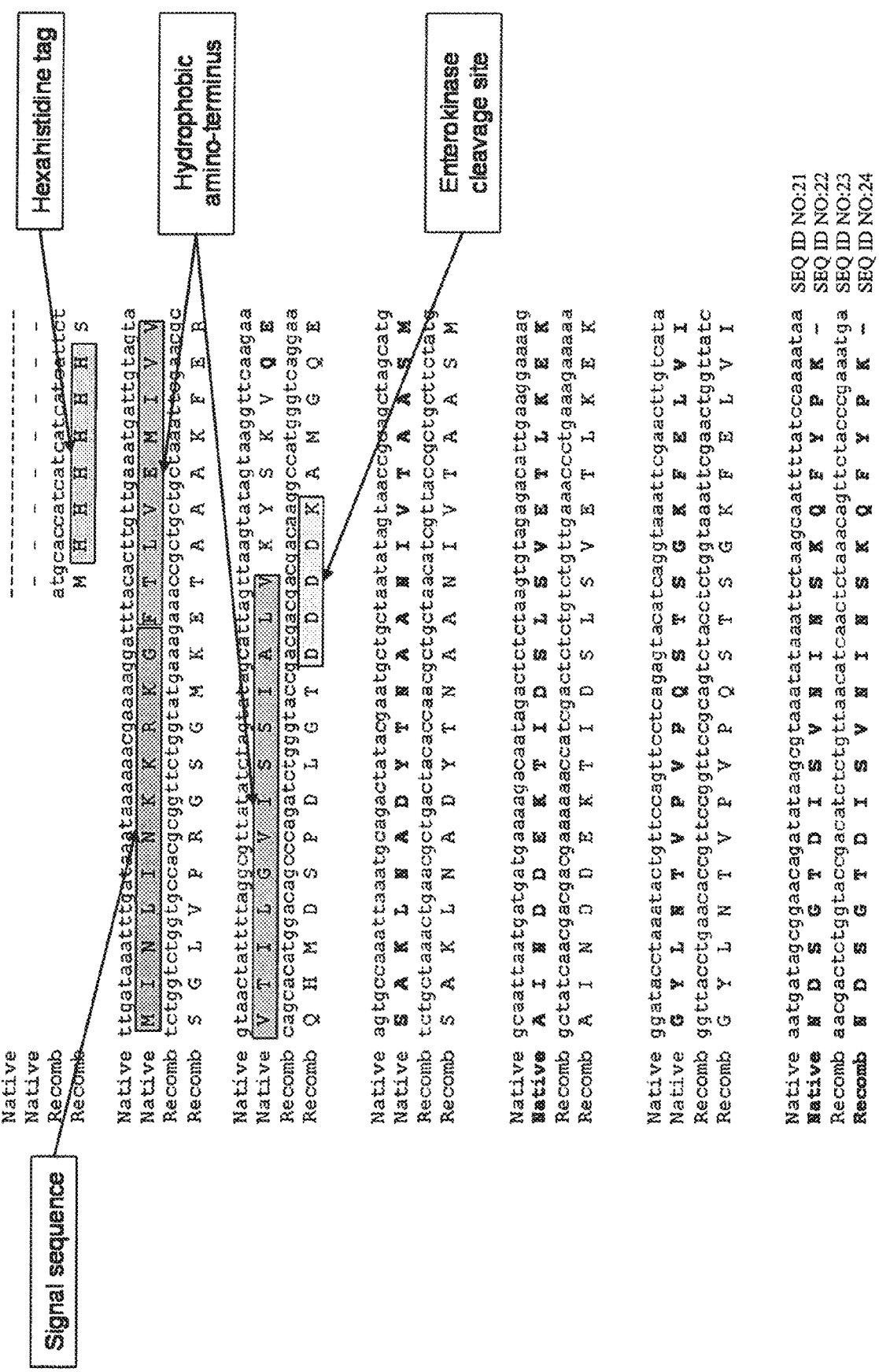

This application is a continuation of U.S. application Ser. No. 13/321,399, now U.S. Pat. No. 8,518,415 which is the U.S. National Stage Application under 35 U.S.C. 371 of International Application No. PCT/US2010/035664, with an international filing date of May 20, 2010, which claims the benefit of U.S. Appl. No. 61/179,747, filed May 20, 2009. The content of the aforesaid application is relied upon and incorporated by reference in its entirety.

REFERENCE TO A SEQUENCE LISTING SUBMITTED ELECTRONICALLY VIA EFS-WEB

The content of the sequence listing (Name: Sequence_listing.txt, Size: 54,093 bytes; and Date of Creation: May 20, 2010) electronically submitted via EFS-Web is incorporated by reference in its entirety.

STATEMENT OF FEDERALLY SPONSORED RESEARCH AND DEVELOPMENT

This invention was made with government support under Grant No. AI037606 awarded by the National Institutes of Health. The government has certain rights in the invention.

FIELD OF THE INVENTION

The present invention generally relates at least to the fields of molecular biology, immunology, infectious disease and medicine. In particular, the invention relates to a *Clostridium difficile* type IV pilin (tfp) gene which can serve as a diagnostic marker for identification of patients infected with *C. difficile* and as a vaccine for therapeutic interventions.

BACKGROUND OF THE INVENTION

*Clostridium difficile* associated disease (CDAD) is a dangerous emerging infection caused by an anaerobic, spore-forming *bacillus* that often threatens the health of elderly patients in various healthcare setting following antibiotic treatments of unrelated infections. CDAD symptoms range in severity from asymptomatic carriage, through mild diarrhea, to a more severe pseudomembranous colitis which can be fatal. The epidemiology of CDAD has been changing dramatically. Formerly found almost exclusively as a complication of antimicrobial therapy among the elderly and infirm in inpatient settings, CDAD has been reported increasingly in outpatients, among otherwise healthy individuals including children, and even in the absence of antimicrobial therapy. Deaths attributable to CDAD have quadrupled in the United States from 5.7 per million persons in 1999 to 23.7 per million in 2004. Redelings M D, Sorvillo F, Mascola L. Increase in *Clostridium difficile*-related mortality rates, United States, 1999-2004. *Emerg Infect Dis.* 2007; 13:1417-9. Estimates of the cost for treatment for CDAD in the United States have been dramatically revised upward from $1 billion in 2002 to $3.2 billion in 2007 due to a dramatic increase in the number of cases and increasing severity of the disease.

The mechanisms by which *C. difficile* colonizes the human colon are not established. A surface protein layer has been described which appears to play a role in binding to tissue culture cells in vitro, but its role in vivo has not been established. Calabi, E., Calabi, F., Phillips, A. D. & Fairweather, N. Binding of *Clostridium difficile* surface layer proteins to gastrointestinal tissues. *Infect Immun* (2002):70:5770-5778. Enterotoxins A (TcdA) and B (TcdB) are the primary virulence factors of *C. difficile*. They are exoenzymes that monoglucosylate small Rho-like GTPases, ultimately leading to the disruption of the actin cytoskeleton of colonic intestinal epithelial cells, destruction of tight junction, and apoptosis. Release of cytokines from intoxicated target cells also leads to massive infiltration of neutrophils into damaged tissue regions, a hallmark of pseudomembranous colitis.

Although primary CDAD can usually be successfully treated with metronidazole or vancomycin, metronidazole resistance and refractory infections are becoming increasingly common. Furthermore, many patients suffer recurrent episodes of CDAD, which can be extremely distressing and difficult to manage. An effective vaccine against CDAD is urgently needed for primary and secondary (relapse) prevention. No licensed vaccine is currently available for CDAD. The approach to vaccination that has advanced furthest into clinical trials has targeted only the *C. difficile* enterotoxins. Toxoid preparations of toxin A and B have completed phase I trials, with both serum free and fecal antibody against both toxins being demonstrated. Kotloff K L, Wasserman S S, Losonsky G A, Thomas W, Jr., Nichols R, Edelman R, Bridwell M, Monath T P. Safety and immunogenicity of increasing doses of a *Clostridium difficile* toxoid vaccine administered to healthy adults. *Infect. Immun.* 2001 February; 69(2): 988-95. The mechanisms by which serum antibody responses are effective against infection and disease caused by *C. difficile* are unclear, although it has been proposed that entry of IgG antitoxin from the blood into mucosal tissues of the large bowel or intestinal lumen may prevent toxin binding.

Type W pili (Tfp) or fimbriae are hair-like surface appendages produced by many species of Gram negative bacteria including *Pseudomonas aeruginosa, Vibrio cholerae, Neisseria gonorrhoeae, N. meningitidis, Salmonella enterica* serovar *Typhi* (herein designated *S. typhi*), *Legionella pneumophila*, enteropathogenic and enterotoxigenic *Escherichia coli*. Tfp play numerous roles in diverse processes such as cellular adhesion, colonization, twitching motility, biofilm formation, and virulence. Tfp are composed exclusively of primarily of many copies of pilin protein, tightly packed in a helix so that the highly hydrophobic amino-terminus of the pilin is buried in the core of the pilus. Tfp pilins have been used successfully as subunit vaccines for the prevention of several diseases in animals. Lepper A W, Moore L J, Atwell J L, Tennent J M. The protective efficacy of pili from different strains of *Moraxella bovis* within the same serogroup against infectious bovine keratoconjunctivitis. *Vet. Microbiol.* 1992; 32:177-87, Lepper A W D, Atwell J L, Lehrbach P R, Schwartzkoff C L, Egerton J R, Tennent J M. The protective efficacy of cloned *Moraxella bovis* pili in monovalent and multivalent vaccine formulations against experimentally induced infectious bovine keratoconjunctivitis (IBK). *Vet. Microbiol.* 1995; 45:129-38. Stewart D J, Clark B L, Peterson J E, Emery D L, Smith E F, Griffiths D A, O'Donnell I J. The protection given by pilus and whole cell vaccines of *Bacteroides nodosus* strain 198 against ovine foot-rot induced by strains of different serogroups. *Aust. Vet. J.* 1985; 62:153-9. Egerton J R, Cox P T, Anderson B J, Kristo C, Norman M, Mattick J S. Protection of sheep against footrot with a recombinant DNA-based fimbrial vaccine. *Vet. Microbiol.* 1987; 14:393-409. Recently investigators have discovered that *Clostridium perfringens* has the genes for and can produce Tfp; similar genes are present in the *C. difficile* genome. Varga J J, Nguyen V, O'Brien D K, Rodgers K, Walker R A, Melville S B. Type IV pili-dependent gliding motility in the Gram-positive pathogen *Clostridium perfringens* and other *Clostridia. Mol. Microbiol.* 2006 November; 62(3):680-94.

There is a need for a multivalent *C. difficile* subunit vaccine and a diagnostic marker for identification of patients infected with *C. difficile*.

SUMMARY OF THE INVENTION

In one embodiment, the present invention relates to a method of inducing an immune response, comprising administering to a subject in need thereof an immunologically-effective amount of a vaccine comprising a *Clostridium difficile* type IV pilin or an antigenic fragment or variant thereof.

In another embodiment, the present invention relates to a method for overexpression of multiple *C. difficile* type IV pilins in gram negative bacteria including but not limited to *E. coli*. The type IV pili serve as colonization factors and vaccine targets.

In another embodiment, the present invention relates to a method for expressing and purifying high levels of *C. difficile* type IV pilins.

In another embodiment, the present invention relates to novel Type IV pilin proteins of *C. difficile* which exhibit high level expression in the bacteria *E. coli.*

In another embodiment, the present invention relates to novel vaccines for *C. difficile* comprising engineered recombinant *C. difficile* type IV pilins.

In another embodiment, the present invention relates to novel biomarkers for use in *C. difficile* detection in patients with *C. difficile* infections.

In another embodiment, the present invention relates to a method for prevention of *C. difficile* colonization and disease in a subject comprising administering a vaccine comprised of purified type IV pilin proteins to said subject.

In another embodiment, the present invention relates to a method for prevention of *C. difficile* spread among mammalian hosts, such as humans, comprising administering a vaccine comprised of purified type IV pilin proteins to said mammal.

BRIEF DESCRIPTION OF THE FIGURES

FIG. 1. Strategy for modification and purification of *C. difficile* PilA2 type IV pilin. The nucleotide and corresponding amino acid sequences of the native and recombinant pilA2 genes are aligned. The hexahistidine tag, enterokinase cleavage sequences of the recombinant protein, pre-pilin peptidase signal sequence and hydrophobic mature amino terminus of the native protein are boxed.

FIG. 2. Coomassie stained gel of purified *C. difficile* PilA1 and PilA2 proteins. M, molecular size standards are shown in the first lane.

FIG. 3. PilA1 is immunogenic in mice. Geometric mean titers for five mice immunized as described in the text. Data are geometric means and standard errors of triplicate samples from three independent ELISA assays.

DETAILED DESCRIPTION OF THE INVENTION

Multiple Pilin Genes and Alleles Identified in Various Strains of *C. difficile.*

In one aspect, the present invention is directed to an engineered Type IV pilin gene of *C. difficile.*

In accordance with the claimed invention, the type IV pilin can come from any *C. difficile* strain. Examples of *C. difficile* strains include *C. difficile* CD196, *C. difficile* CIP 107932, *C. difficile* QCD-32g58, *C. difficile* QCD-37x79, *C. difficile* QCD-66c26, *C. difficile* QCD-76w55, *C. difficile* QCD-97b34, *C. difficile* R20291, *C. difficile* QCD-63q42, *C. difficile* QCD-23 m63, *C. difficile* 630, and *C. difficile* ATCC 43255.

All of the strains listed above have two to four genes that can be predicted to encode type IV pilin proteins. As used herein, these genes will be referred to as pilA1, pilA2, pilA3 and pilA4. The *C. difficile* strains can harbor allelic variants of the type IV pilins. Alleles of pilA1, as used herein, include pilA1.1, pilA1.2, pilA1.3, pilA1.4 and pilA1.5. Alleles of pilA2, as used herein, include pilA2.1 and pilA2.2. Alleles of pilA3, as used herein, include pilA3.1, pilA3.2 and pilA3.3. Alleles of pilA4, as used herein, include pilA4.1.

Each of these genes is predicted to encode a protein composed of a short, positively charged signal peptide, a prepilin peptidase cleavage site and a hydrophobic mature amino-terminal domain characteristic of Type IVa pilins. Mature pilin proteins are naturally derived from pre-pilin proteins by the action of pre-pilin peptidase enzymes which cleave the signal peptide and N-methylate the mature amino terminus.

PilA1: The mature PilA1 protein is predicted to be 158-164 amino acids long. Eight strains are predicted to express identical PilA1 proteins, while the PilA1 proteins of the other four strains are predicted to be 75%, 89%, 91% and 93% identical to these eight.

PilA1.1 is found in *C. difficile* strains CD196, CIP 107932, QCD-32g58, QCD-37x79, QCD-66c26, QCD-76w55, QCD-97b34 and R20291. The native nucleotide sequence of PilA1.1 is SEQ ID NO:1 and the native amino acid sequence is SEQ ID NO:2.

PilA1.2 is found in *C. difficile* strain QCD-63q42. The native nucleotide sequence of PilA1.2 is SEQ ID NO:5 and the native amino acid sequence is SEQ ID NO:6.

PilA1.3 is found in *C. difficile* strain QCD-23 m63. The native nucleotide sequence of PilA1.3 is SEQ ID NO:9 and the native amino acid sequence is SEQ ID NO:10.

PilA1.4 is found in *C. difficile* strain 630. The native nucleotide sequence of PilA1.4 is SEQ ID NO:13 and the native amino acid sequence is SEQ ID NO:14.

PilA1.5 is found in *C. difficile* strain ATCC 43255. The native nucleotide sequence of PilA1.5 is SEQ ID NO:17 and the native amino acid sequence is SEQ ID NO:18.

The first 9 amino acids of SEQ ID NOS: 2, 6, 10, 14, and 18 comprise pre-pilin leader sequence that is cleaved during processing in *C. difficile.*

PilA2: All 12 strains are predicted to encode a 109-amino acid mature PilA2 protein. The predicted PilA2 protein is identical in 11 of these strains, and 95% identical in the other strain.

PilA2.1 is found in *C. difficile* strains CD196, CIP 107932, QCD-32g58, QCD-37x79, QCD-66c26, QCD-76w55, QCD-97b34, R20291, QCD63q42, 630 and ATCC 43255. The native nucleotide sequence of PilA2.1 is SEQ ID NO:21 and the native amino acid sequence is SEQ ID NO:22. The first 11 amino acids of SEQ ID NO:22 comprise pre-pilin leader sequence that is cleaved during processing to yield the mature protein.

PilA2.2 is found in *C. difficile* strain QCD-23 m63. The native nucleotide sequence of PilA2.2 is SEQ ID NO:25 and the native amino acid sequence is SEQ ID NO:26. The first 8 amino acids of SEQ ID NO:26 comprise pre-pilin leader sequence that is cleaved during processing to yield the mature protein.

PilA3: The pilA3 gene is present in 11 of the 12 strains and is predicted to encode a protein closely related at its amino terminus to PilA1. Forty-two of the first 57 amino acids of all PilA1 and PilA3 predicted mature proteins are identical. However, the sequence similarities between PilA1 and PilA3 end abruptly at that point. The predicted mature PilA3 proteins are 156-159 amino acids long. Seven strains are predicted to express identical PilA3 proteins, two additional strains are predicted to encode identical PilA3 proteins that are 76% identical to these seven and one strain is predicted to encode a PilA3 protein 95% identical to those of the majority.

PilA3.1 is found in *C. difficile* strains CD196, CIP 107932, QCD-32g58, QCD-37x79, QCD-66c26, QCD-76w55, QCD-97b34 and R20291. The native nucleotide sequence of PilA3.1 is SEQ ID NO:29 and the native amino acid sequence is SEQ ID NO:30.

PilA3.2 is found in *C. difficile* strain 630. The native nucleotide sequence of PilA3.2 is SEQ ID NO:33 and the native amino acid sequence is SEQ ID NO:34.

PilA3.3 is found in *C. difficile* strains QCD-63q42 and ATCC 43255. The native nucleotide sequence of PilA3.3 is SEQ ID NO:37 and the native amino acid sequence is SEQ ID NO:38.

The first 6 amino acids of SEQ ID NOS:30, 34 and 38 comprise pre-pilin leader sequence that is cleaved during processing to yield the mature proteins.

PilA4: The gene encoding the PilA4 protein is present in only 3 strains and is predicted to encode an identical 263 amino acid protein. PilA4.1 is found in *C. difficile* strains CD196, QCD32g58 and R20291. The native nucleotide sequence of PilA4.1 is SEQ ID NO:41 and the native amino acid sequence is SEQ ID NO:42. The first 10 amino acids of SEQ ID NO:42 comprise pre-pilin leader sequence that is cleaved during processing to yield the mature protein.

In total, one strain has only two pilA genes, eight strains have three pilA genes and three strains have four.

Vectors, Host Cells, Recombinant Expression, Polypeptides, Antigenic Fragments and Variants.

In some embodiments, the present invention relates to vectors that comprise a type IV pilin polynucleotide from *C. difficile*, host cells which are genetically engineered to express type IV pilins and the production of polypeptides of the invention by recombinant techniques. Cell-free translation systems can also be employed to produce such proteins using RNAs derived from the DNA constructs of the invention.

When a polynucleotide encoding a type IV pilin of *C. difficile* is used for the recombinant production of a polypeptide, the polynucleotide may include the coding sequence for the full-length polypeptide or an antigenic fragment thereof, by itself; the coding sequence for the full-length polypeptide or fragment in reading frame with other coding sequences, such as those encoding a leader or secretory sequence, a pre-, or pro or preprotein sequence, or other fusion peptide portions. For example, a marker sequence that facilitates purification of the fused polypeptide can be encoded. In certain embodiments of this aspect of the invention, the marker sequence is a hexa-histidine peptide, for example, as provided in the pQE vector (Qiagen, Inc.) and described in Gentz et al., *Proc Natl Acad Sci USA* 86:821-824 (1989), or it may be the HA tag, which corresponds to an epitope derived from the influenza hemagglutinin protein (Wilson, I., et al., Cell 37:767, 1984). The polynucleotide may also contain non-coding 5' and 3° sequences, such as transcribed, non-translated sequences, ribosome binding sites and sequences that stabilize mRNA.

Representative examples of appropriate hosts include bacterial cells, such as *streptococci, staphylococci, E. coli, Streptomyces, Bacillus subtilis*, and *Salmonella enterica typhi* cells; fungal cells, such as yeast cells and *Aspergillus* cells. In some embodiments, gram negative bacteria are the host cells. A great variety of expression systems can be used, including DNA or RNA vectors.

In other embodiments, the invention provides an isolated nucleic acid molecule comprising a type IV pilin operably linked to a heterologous promoter. In some embodiments, the invention further provides an isolated nucleic acid molecule comprising a type IV pilin operably linked to a heterologous promoter, wherein said isolated nucleic acid molecule is capable of expressing a type IV pilin polypeptide when used to transform an appropriate host cell.

In some embodiments, the invention relates to an isolated nucleic acid molecule encoding an antigenic fragment of type IV pilin linked to an affinity tag sequence and enzymatic cleavage sequence to facilitate purification. In some embodiments, the affinity tag is a 6×-Histidine tag and the cleavage sequence is recognized by enterokinase. In some embodiments, the nucleic acid molecules are optimized to increase expression in *E. coli* without altering the amino acid sequence using preferred codons in *E. coli*.

In some embodiments, the present invention is directed to purified polypeptides, variants and antigenic fragments of a type IV pilin of *C. difficile*. In some embodiments, the type N pilin is engineered to lack the native leader sequence and amino terminal hydrophobic domain.

In some embodiments, the type N pilin polypeptides of the present invention include the polypeptides of SEQ ID NO:2, SEQ ID NO:6, SEQ ID NO:10, SEQ ID NO:14, SEQ ID NO:18, SEQ ID NO:22, SEQ ID NO:26, SEQ ID NO:30, SEQ ID NO:34, SEQ ID NO:38 and SEQ ID NO:42 as well as antigenic fragments and variants which have at least 90% identity thereto. In some embodiments, the polypeptides have at least 96%, 97% or 98% identity to the polypeptides of SEQ ID NO:2, SEQ ID NO:6, SEQ ID NO:10, SEQ ID NO:14, SEQ ID NO:18, SEQ ID NO:22, SEQ ID NO:26, SEQ ID NO:30, SEQ ID NO:34, SEQ ID NO:38, SEQ ID NO:42 and antigenic fragments thereof. In some embodiments, the polypeptides have at least 91%, 92%, 93%, 94%, 95%, 96%, 97%, 98%, 99%, or 100% identity to the polypeptide of SEQ ID NO:2, SEQ ID NO:6, SEQ ID NO:10, SEQ ID NO:14, SEQ ID NO:18, SEQ ID NO:22, SEQ ID NO:26, SEQ ID NO:30, SEQ ID NO:34, SEQ ID NO:38 and SEQ ID NO:42 and antigenic fragments thereof.

In some embodiments, the variant polypeptides, including those which have 90% or more identity to the type IV pilins described herein or antigenic fragments thereof, are recognized by an antibody that binds a polypeptide selected from the group consisting of SEQ NO:2, SEQ ID NO:6, SEQ ID NO:10, SEQ ID NO:14, SEQ ID NO:18, SEQ ID NO:22, SEQ ID NO:26, SEQ ID NO:30, SEQ ID NO:34, SEQ ID NO:38, SEQ ID NO:42 and antigenic fragments thereof. In some embodiments, the invention is directed to a variant having 90%, 91%, 92%, 93%, 94%, 95%, 96%, 97%, 98%, 99% or more identity to a type IV pilin described herein and is recognized by an antibody that binds a type IV pilin antigenic fragment selected from the group consisting of amino acids 35-173 of SEQ NO:2, amino acids 35-173 of SEQ ID NO:6, amino acids 35-173 of SEQ ID NO:10, amino acids 35-171 of SEQ ID NO:14, amino acids 35-170 of SEQ ID NO:18, amino acids 34-119 of SEQ ID NO:22, amino acids 31-116 of SEQ ID NO:26, amino acids 32-164 of SEQ ID NO:30, amino acids 32-164 of SEQ ID NO:34, amino acids 32-162 of SEQ ID NO:38, and amino acids 36-272 of SEQ ID NO:42.

In some embodiments, the type IV pilin polypeptides, variants or antigenic fragments are part of a larger protein such as a fusion protein. It is often advantageous to include additional amino acid sequence which contains secretory or leader sequences, pro-sequences, sequences which aid in purification such as multiple histidine residues, or additional sequence for stability during recombinant production.

An antigenic fragment is a polypeptide having an amino acid sequence that entirely is the same as part but not all of the amino acid sequence of one of the aforementioned type IV pilin polypeptides. The antigenic fragment can be "freestanding," or comprised within a larger polypeptide of which they form a part or region, most preferably as a single continuous region.

In some embodiments, the antigenic fragments include, for example, truncation polypeptides having the amino acid sequence of the type IV pilin polypeptides, except for deletion of a continuous series of residues that includes the amino terminus, or a continuous series of residues that includes the carboxyl terminus or deletion of two continuous series of residues, one including the amino terminus and one including the carboxyl terminus. In some embodiments, fragments are characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, and high antigenic index regions.

The antigenic fragment can be of any size. In some embodiments the fragment is capable of inducing an immune response in a subject or be recognized by a specific antibody. In some embodiments, the fragment corresponds to an amino-terminal truncation mutant. In some embodiments, the number of amino terminal amino acids missing from the fragment ranges from 1-100 amino acids. In some embodiments, it ranges from 1-75 amino acids, 1-50 amino acids, 1-40 amino acids, 1-30 amino acids, 1-25 amino acids, 1-20 amino acids, 1-15 amino acids, 1-10 amino acids and 1-5 amino acids.

In some embodiments, the fragment corresponds to carboxyl-terminal truncation mutant. In some embodiments, the number of carboxyl terminal amino acids missing from the fragment ranges from 1-100 amino acids. In some embodiments, it ranges from 1-75 amino acids, 1-50 amino acids, 1-40 amino acids, 1-30 amino acids, 1-25 amino acids, 1-20 amino acids, 1-15 amino acids, 1-10 amino acids and 1-5 amino acids.

In some embodiments, the fragment corresponds to an internal fragment that lacks both the amino and carboxyl terminal amino acids. In some embodiments, the fragment is 7-200 amino acid residues in length. In some embodiments, the fragment is 10-100 amino acid residues, 15-85 amino acid residues, 25-65 amino acid residues or 30-50 amino acid residues in length. In some embodiments, the fragment is 7 amino acids, 10 amino acids, 12 amino acids, 15 amino acids, 20 amino acids, 25 amino acids, 30 amino acids, 35 amino acids, 40 amino acids, 45 amino acids, 50 amino acids 55 amino acids, 60 amino acids, 80 amino acids or 100 amino acids in length.

Of course larger antigenic fragments are also useful according to the present invention, as are fragments corresponding to most, if not all, of the amino acid sequence of SEQ ID NO:2, SEQ ID NO:6, SEQ ID NO:10, SEQ ID NO:14, SEQ ID NO:18, SEQ ID NO:22, SEQ ID NO:26, SEQ ID NO:30, SEQ ID NO:34, SEQ ID NO:38 and SEQ ID NO:42.

In some embodiments, the antigenic fragment is selected from the group consisting of a peptide comprising amino acids 35-173 of SEQ ID NO:2, amino acids 35-173 of SEQ ID NO:6, amino acids 35-173 of SEQ ID NO:10, amino acids 35-171 of SEQ ID NO:14, amino acids 35-170 of SEQ ID NO:18, amino acids 34-119 of SEQ ID NO:22, amino acids 31-116 of SEQ ID NO:26, amino acids 32-164 of SEQ ID NO:30, amino acids 32-164 of SEQ ID NO:34, amino acids 32-162 of SEQ ID NO:38, and amino acids 36-272 of SEQ ID NO:42.

Thus, the polypeptides of the invention include polypeptides having an amino acid sequence at least 90% identical to that of SEQ ID NO:2, SEQ ID NO:6, SEQ ID NO:10, SEQ ID NO:14, SEQ ID NO:18, SEQ ID NO:22, SEQ ID NO:26, SEQ ID NO:30, SEQ ID NO:34, SEQ ID NO:38 and SEQ ID NO:42 or antigenic fragments thereof. In some embodiments, the variants are those that vary from the reference by conservative amino acid substitutions, i.e., those that substitute a residue with another of like characteristics. Typical substitutions are among Ala, Val, Leu and Ile; among Ser and Thr; among the acidic residues Asp and Glu; among Asn and Gln; and among the basic residues Lys and Arg, or aromatic residues Phe and Tyr. In some embodiments, the polypeptides are variants in which several, 5 to 10, 1 to 5, or 1 to 2 amino acids are substituted, deleted, or added in any combination.

The type IV pilin polypeptides, variants and antigenic fragments of the invention can be prepared in any suitable manner. Such polypeptides include isolated naturally occurring polypeptides, recombinantly produced polypeptides, synthetically produced polypeptides, or polypeptides produced by a combination of these methods.

In some embodiments, the invention is directed to engineered type IV pilin which is optimized for high level expression in *E. coli* using codons that are preferred in *E. coli*. In some embodiments, the invention is directed to engineered antigenic fragments of type IV pilin of *C. difficile* (nucleic acid and amino acid sequences), which are optimized for expression in *E. coli*, and harbor a histidine tag and enterokinase cleavage site to facilitate purification of the protein. In some embodiments, the fragments lack the pre-pilin leader sequence and hydrophobic domain found in the native proteins.

In some embodiments, the codons are optimized for high level expression in *E. coli*. As used herein, a codon that is "optimized for high level expression in *E. coli*" refers to a codon that is relatively more abundant in *E. coli* in comparison with all other codons corresponding to the same amino acid. In some embodiments, at least 40% of the codons are optimized for high level expression in *E. coli*. In some embodiments, at least 50%, at least 60%, at least 70%, at least 80%, at least 85%, at least 90%, at least 95%, or at least 99% of the codons are optimized for high level expression in *E. coli*.

The following sequences are optimized for expression in *E. coli* and also are fused to histidine tags and enterokinase cleavage sites.

SEQ ID NO:3 is a nucleotide sequence comprising an antigenic fragment encoding amino acids 35-173 of PilA1.1. The amino acid sequence encoded by SEQ ID NO:3 is SEQ ID NO:4.

SEQ ID NO:7 is a nucleotide sequence comprising an antigenic fragment encoding amino acids 35-173 of PilA1.2. The amino acid sequence encoded by SEQ ID NO:7 is SEQ ID NO:8.

SEQ ID NO:11 is a nucleotide sequence comprising an antigenic fragment encoding amino acids 35-173 of PilA1.3. The amino acid sequence encoded by SEQ ID NO:11 is SEQ ID NO:12.

SEQ ID NO:15 is a nucleotide sequence comprising an antigenic fragment encoding amino acids 35-171 of PilA1.4. The amino acid sequence encoded by SEQ ID NO:15 is SEQ ID NO:16.

SEQ ID NO:19 is a nucleotide sequence comprising an antigenic fragment encoding amino acids 35-170 of PilA1.5. The amino acid sequence encoded by SEQ ID NO:19 is SEQ ID NO:20.

SEQ ID NO:23 is a nucleotide sequence comprising an antigenic fragment encoding amino acids 34-119 of PilA2.1. The amino acid sequence encoded by SEQ ID NO:23 is SEQ ID NO:24.

SEQ ID NO:27 is a nucleotide sequence comprising an antigenic fragment encoding amino acids 31-116 of PilA2.2. The amino acid sequence encoded by SEQ ID NO:27 is SEQ ID NO:28.

SEQ NO:31 is a nucleotide sequence comprising an antigenic fragment encoding amino acids 32-164 of PilA3.1. The amino acid sequence encoded by SEQ ID NO:31 is SEQ ID NO:32.

SEQ ID NO:35 is a nucleotide sequence comprising an antigenic fragment encoding amino acids 32-164 of PilA3.2. The amino acid sequence encoded by SEQ ID NO:35 is SEQ ID NO:36.

SEQ ID NO:39 is a nucleotide sequence comprising an antigenic fragment encoding amino acids 32-162 of PilA3.3. The amino acid sequence encoded by SEQ ID NO:39 is SEQ ID NO:40.

SEQ ID NO:43 is a nucleotide sequence comprising an antigenic fragment encoding amino acids 36-272 of PilA4.1. The amino acid sequence encoded by SEQ ID NO:43 is SEQ ID NO:44.

In accordance with the invention, such polypeptides and fragments are useful as immunogens and also as diagnostic tools to aid in the detection of antibodies that react with type IV pilin of *C. difficile* from a biological sample from a subject suspected of being infected, or at risk for infection, previously infected or immunized with a type IV pilin immunogen.

Methods of Inducing an Immune Response.

The present invention also includes methods of inducing an immune response comprising administering to a subject in need thereof an immunologically-effective amount of a vaccine comprising *Clostridium difficile* type IV pilin or an antigenic fragment or variant thereof.

In certain aspects of the invention, the vaccine is administered alone in a single dose or administered in sequential doses.

In some embodiments, a combination of *C. difficile* type IV pilins or antigenic fragments or variants thereof is administered, to provide protection against a broad spectrum of *C. difficile* strains, or particular strains that are more prevalent. In some embodiments, the combination is administered as a single, multivalent vaccine composition. In other embodiments, the type IV pilins or antigenic fragments or variants thereof are administered in more than one vaccine composition.

In some embodiments, a type IV pilin or antigenic fragment or variant thereof is conjugated, either genetically or chemically to one or more type IV pilins or antigenic fragments or variants thereof, another *C. difficile* antigen, a bacterial antigen, toxin or the like, and administered as a conjugate vaccine.

In some embodiments, one of the following combinations is administered: a combination comprising one or more PilA1, one or more PilA2, one or more PilA3 and one or more PilA4 proteins, variants or antigenic fragment thereof, a combination comprising one or more PilA1, one or more PilA2, one or more PilA3 proteins, variants or antigenic fragments thereof, a combination comprising one or more PilA1, one or more PilA2, one or more PilA4 proteins, variants or antigenic fragments thereof, a combination comprising one or more PilA1, one or more PilA3, one or more PilA4 proteins, variants or antigenic fragments thereof, a combination comprising one or more PilA2, one or more PilA3, one or more PilA4 proteins, variants or antigenic fragments thereof, a combination comprising one or more PilA1 and one or more PilA2 proteins, variants or antigenic fragments thereof, a combination comprising one or more PilA1 and one or more PilA3 proteins, variants or antigenic fragments thereof, a combination comprising one or more PilA1 and one or more PilA4 proteins, variants or antigenic fragments thereof, a combination comprising one or more PilA2 and one or more PilA3 proteins, variants or antigenic fragments thereof, a combination comprising one or more PilA2 and one or more PilA4 proteins, variants or antigenic fragments thereof, and a combination comprising one or more PilA3 and one or more PilA4 proteins, variants or antigenic fragments thereof.

In some embodiments, PilA1 comprises a peptide selected from the group consisting of a PilA1.1 antigenic fragment (amino acids amino acids 35-173 of SEQ ID NO:2), a PilA1.2 antigenic fragment (amino acids amino acids 35-173 of SEQ ID NO:6), a PilA1.3 antigenic fragment (amino acids amino acids 35-173 of SEQ ID NO:10), a PilA1.4 antigenic fragment (amino acids 35-171 of SEQ NO:14), a PilA1.5 antigenic fragment (amino acids 35-170 of SEQ ID NO:18) and combinations thereof. In some embodiments, PilA1 includes all the PilA1 allele fragments listed above.

In some embodiments, PilA2 comprises a peptide selected from the group consisting of a PilA2.1 antigenic fragment (amino acids 34-119 of SEQ ID NO: 22), a PilA2.2 antigenic fragment (amino acids 31-116 of SEQ ID NO:26) and combinations thereof. In some embodiments, PilA2 includes all the PilA2 allele fragments listed above.

In some embodiments, PilA3 comprises a peptide selected from the group consisting of a PilA3.1 antigenic fragment (amino acids 32-164 of SEQ ID NO: 30), a PilA3.2 antigenic fragment (amino acids 32-164 of SEQ ID NO:34), a PilA3.3 antigenic fragment (amino acids 32-162 of SEQ ID NO:38) and combinations thereof. In some embodiments, PilA3 includes all the PilA3 allele fragments listed above.

In some embodiments, PilA4 comprises a peptide selected from the group consisting of a PilA4.1 antigenic fragment (amino acids 36-272 of SEQ ID NO: 42).

In some embodiments, the type IV pilin is from a *C. difficile* strain selected from the group consisting of *C. difficile* CD196, *C. difficile* CIP 107932, *C. difficile* QCD-32g58, *C. difficile* QCD-37x79, *C. difficile* QCD-66c26, *C. difficile* QCD-76w55, *C. difficile* QCD-97b34, *C. difficile* R20291, *C. difficile* QCD-63q42, *C. difficile* QCD-23 m63, *C. difficile* 630, *C. difficile* ATCC 43255 and combinations thereof.

In some embodiments, the type IV pilin is selected from the group consisting of SEQ ID NO:2; SEQ ID NO:6; SEQ ID NO:10; SEQ ID NO:14; SEQ ID NO:18; SEQ ID NO:22; SEQ ID NO:26; SEQ ID NO:30; SEQ ID NO:34; SEQ ID NO:38; SEQ ID NO:42, variants thereof, antigenic fragments thereof, and combinations thereof.

In some embodiments, a combination of PilA1 type IV pilin is administered. In some embodiments, one of the following combinations is administered: a combination comprising SEQ ID NO:2, variants or antigenic fragments thereof; a combination comprising SEQ ID NO:6, variants or antigenic fragments thereof; a combination comprising SEQ ID NO:10, variants or antigenic fragments thereat a combination comprising SEQ ID NO:14, variants or antigenic fragments thereof; and a combination comprising SEQ ID NO:18, variants or antigenic fragments thereof.

In some embodiments, a combination of SEQ ID NO:2, SEQ ID NO:6, SEQ ID NO:10, SEQ ID NO:14 and SEQ ID NO:18, variants or antigenic fragments thereof is administered.

In some embodiments, the combination comprises at least four type IV pilins. In some embodiments, the type IV pilins are PilA1 alleles, variants or antigenic fragments thereof. In some embodiments, one of the following combinations is administered: a combination of SEQ ID NO:2, SEQ ID NO:6, SEQ ID NO:10 and SEQ ID NO:18 or variants or antigenic fragments thereof; a combination of SEQ ID NO:2, SEQ ID NO:6, SEQ ID NO:10 and SEQ ID NO:14, or variants or antigenic fragments thereof; a combination of SEQ ID NO:2, SEQ ID NO:10, SEQ ID NO:14 and SEQ ID NO:18 or variants or antigenic fragments thereof; a combination of SEQ ID NO:2, SEQ ID NO:6, SEQ ID NO:14 and SEQ ID NO:18 or variants or antigenic fragments thereof; and a combination of SEQ NO:6, SEQ ID NO:10, SEQ ID NO:14 and SEQ ID NO:18 or variants or antigenic fragments thereof.

In some embodiments, the combination comprises at least three type IV pilins. In some embodiments, the type IV pilins are PilA1 alleles, variants or antigenic fragments thereof. In some embodiments, one of the following combinations is administered: a combination of SEQ ID NO:2, SEQ ID NO:6 and SEQ ID NO:10, or variants or antigenic fragments thereof; a combination of SEQ ID NO:2, SEQ ID NO:6 and SEQ ID NO:14, or variants or antigenic fragments thereof; a combination of SEQ ID NO:2, SEQ ID NO:6 and SEQ ID NO:18, or variants or antigenic fragments thereof; a combination of SEQ ID NO:2, SEQ ID NO:10 and SEQ ID NO:14, or variants or antigenic fragments thereof; a combination of SEQ ID NO:2, SEQ ID NO:10 and SEQ ID NO:18, or variants or antigenic fragments thereof; a combination of SEQ ID NO:2, SEQ ID NO:14 and SEQ ID NO:18, or variants or antigenic fragments thereof; a combination of SEQ ID NO:6, SEQ ID NO:10 and SEQ ID NO:14, or variants or antigenic fragments thereof; a combination of SEQ ID NO:6, SEQ ID NO:10 and SEQ ID NO:18, or variants or antigenic fragments thereof; a combination of SEQ ID NO:6, SEQ ID NO:14 and SEQ ID NO:18, or variants or antigenic fragments thereof; and a combination of SEQ ID NO:10, SEQ ID NO:14 and SEQ ID NO:18, or variants or antigenic fragments thereof.

In some embodiments, the combination comprises at least three type IV pilins that are PilA3 alleles, variants or antigenic fragments thereof. In some embodiments, a combination of SEQ ID NO:30, SEQ ID NO:34 and SEQ ID NO:38, or variants or antigenic fragments thereof is administered. In some embodiments, the combination comprises at least two type IV pilins. In some embodiments, the type IV pilins are PilA1 alleles, variants or antigenic fragments thereof. In some embodiments, one of the following combinations is administered: a combination of SEQ ID NO:2 and SEQ ID NO:6, or variants or antigenic fragments thereof; a combination of SEQ ID NO:2 and SEQ ID NO:10, or variants or antigenic fragments thereof; a combination of SEQ ID NO:2 and SEQ NO:14, or variants or antigenic fragments thereof; a combination of SEQ ID NO:2 and SEQ ID NO:18, or variants or antigenic fragments thereof; a combination of SEQ ID NO:6 and SEQ ID NO:10, or variants or antigenic fragments thereof; a combination of SEQ ID NO:6 and SEQ ID NO:14, or variants or antigenic fragments thereof; a combination of SEQ ID NO:6 and SEQ ID NO:18, or variants or antigenic fragments thereof; a combination of SEQ ID NO:10 and SEQ ID NO:14, or variants or antigenic fragments thereof; a combination of SEQ ID NO:10 and SEQ ID NO:18, or variants or antigenic fragments thereof; and a combination of SEQ ID NO:14 and SEQ ID NO:18, or variants or antigenic fragments thereof.

In some embodiments, the combination comprises at least two type IV pilins that are PilA2 alleles, variants or antigenic fragments thereof. In some embodiments, a combination of SEQ ID NO:22 and SEQ NO:26 or variants or antigenic fragments thereof is administered.

In some embodiments, the combination comprises at least two type IV pilins that are PilA3 alleles, variants or antigenic fragments thereof. In some embodiments, one of the following combinations is administered: a combination of SEQ ID NO:30 and SEQ ID NO:34 or variants or antigenic fragments thereof; a combination of SEQ ID NO:30 and SEQ ID NO:38, or variants or antigenic fragments thereof; and a combination of SEQ ID NO:34 and SEQ ID NO:38 or variants or antigenic fragments thereof.

In some embodiments, a combination comprising a PilA1, PilA2, PilA3 and PilA4 protein, variant or antigenic fragment thereof is administered.

In some embodiments, the antigenic fragment of the PILA1 protein comprises a peptide selected from the group consisting of amino acids 35-173 of SEQ ID NO:2; amino acids 35-173 of SEQ ID NO:6; amino acids 35-173 of SEQ ID NO:10; amino acids 35-171 of SEQ ID NO:14; amino acids 35-170 of SEQ ID NO:18 and combinations thereof.

In some embodiments, the antigenic fragment of the PILA2 protein comprises a peptide selected from the group consisting of: amino acids 34-119 of SEQ ID NO:22; amino acids 31-116 of SEQ ID NO:26 and combinations thereof.

In some embodiments, the antigenic fragment of the PILA3 protein comprises a peptide selected from the group consisting of: amino acids 32-164 of SEQ ID NO:30; amino acids 32-164 of SEQ ID NO:34; amino acids 32-162 of SEQ ID NO:38; and combinations thereof.

In some embodiments, the antigenic fragment of the PILA4 protein comprises amino acids 36-272 of SEQ ID NO:42.

In some embodiments, the type IV pilins, variants or antigenic fragments thereof for use in the methods of the invention are recombinantly produced. In some embodiments, the type IV pilins, variants or antigenic fragments thereof are produced in E. coli using genetically engineered nucleic acids optimized for high level expression using preferred E. coli codons.

As used herein, an immunologically-effective amount is an amount sufficient to induce an immune response in the subject.

As used herein, an "immune response" is the physiological response of the subject's immune system to an immunizing composition. An immune response may include an innate immune response, an adaptive immune response, or both. In some embodiments of the present invention, the immune response is a protective immune response. A protective immune response confers immunological cellular memory upon the subject, with the effect that a secondary exposure to the same or a similar antigen is characterized by one or more of the following characteristics: shorter lag phase than the lag phase resulting from exposure to the selected antigen in the absence of prior exposure to the immunizing composition; production of antibody which continues for a longer period than production of antibody resulting from exposure to the selected antigen in the absence of prior exposure to the immunizing composition; a change in the type and quality of antibody produced in comparison to the type and quality of antibody produced upon exposure to the selected antigen in the absence of prior exposure to the immunizing composition; a shift in class response, with IgG antibodies appearing in higher concentrations and with greater persistence than IgM, than occurs in response to exposure to the selected antigen in the absence of prior exposure to the immunizing composition; an increased average affinity (binding constant) of the antibodies for the antigen in comparison with the average affinity of antibodies for the antigen resulting from exposure to the selected antigen in the absence of prior exposure to the immunizing composition; and/or other characteristics known in the art to characterize a secondary immune response.

In some embodiments, the vaccines of the invention are administered with a pharmaceutically acceptable carrier, such that it provides host immunity against an infection.

The term "carrier" denotes an organic or inorganic ingredient, natural or synthetic, with which the active ingredient is combined to facilitate the application of the vaccine. The characteristics of the carrier depend on the nature of the vaccine and the route of administration. Physiologically and pharmaceutically-acceptable carriers include diluents, fillers, salts, buffers, stabilizers, solubilizers, and other materials. The term "pharmaceutically acceptable" is used to refer to a non-toxic material that is compatible with a biological system such as a cell, cell culture, tissue, or organism.

In practicing immunization protocols for treatment and/or prevention, an immunologically-effective amount of type IV pilin or a variant or antigenic fragment thereof is administered to a subject. The particular dosage depends upon the age, weight, sex and medical condition of the subject to be treated, as well as on the method of administration.

The vaccines of the invention can be administered by either single or multiple dosages of an effective amount. In some embodiments, an effective amount of the type IV pilin of the invention can vary from 0.01-5,000 µg/ml per dose. In other embodiments, an effective amount of the type IV pilin can vary from 0.1-500 µg/ml per dose, and in other embodiments, it can vary from 10-300 µg/ml per dose. In one embodiment, the dosage of type IV pilin will range from about 10 µg to about 1000 µg. In another embodiment, the amount administered will be between about 20 µg and about 500 µg. In some embodiments, the amount administered will be between about 75 µg and 250 µg. Greater doses may be administered on the basis of body weight. The exact dosage can be determined by routine dose/response protocols known to one of ordinary skill in the art.

In some embodiments, the amount of the type IV pilin that provides an immunologically-effective amount for vaccination against infection is from about 1 µg or less to about 5000 pig or more. In some embodiments, it is from about 2, 3, 4, 5, 6, 7, 8, 9, 10, 15, 20, 25, 30, 35, 40, 45 or 50 µg is to about 55, 60, 65, 70, 75, 80, 85, 90, or 95 µg per kg body weight. In one embodiment, the immunologically-effective amount for vaccination against bacterial infection is from 10 µg to 1000 µg.

The term "subject" as used herein, refers to animals, such as mammals. For example, mammals contemplated include humans, primates, dogs, cats, sheep, cattle, goats, pigs, horses, chickens, mice, rats, rabbits, guinea pigs, and the like. The teems "subject", "patient", and "host" are used interchangeably.

In some embodiments, the subject is a human. In some embodiments, the subjects are patients who are at high risk of C. difficile infections. In some embodiments, the subjects are selected from the group consisting of elderly patients in healthcare or nursing care settings, patients who have undergone antibiotic treatment of unrelated infections, are currently undergoing antibiotic treatment or are about to undergo antibiotic treatment, patients in healthcare settings, patients who have previously been infected with C. difficile or who have experienced CDAD symptoms. In some embodiments, the subjects are outpatients. In some embodiments, the subjects are healthy individuals. In some embodiments, the subjects are at risk of C. difficile infection because of their close contact with an infected individual or exposure to surroundings that might be infected with C. difficile or infection causing spores thereof.

In some embodiments, the subjects include patients that have received broad spectrum antibiotics, such as hospitalized elderly patients, nursing home residents, chronically ill patients, cancer patients, AIDS patients, patients in intensive care units, and patients receiving dialysis treatment.

The vaccine of the present invention may confer resistance to Clostridium difficile by either passive immunization or active immunization. In one embodiment of passive immunization, the vaccine is provided to a subject (i.e. a human or mammal), and the elicited antisera is recovered and directly provided to a recipient suspected of having an infection caused by C. difficile.

In some embodiments of passive immunization, the C. difficile immune globulin is administered in amounts ranging from 100 µg/kg-100 mg/kg, or 1-50 g/kg, for example, about 15 mg/kg, depending on donor titer. The immune globulin can be administered in, e.g., one or two doses. an initial dose can be administered for treatment and a second dose can be administered to prevent relapse.

The administration of the vaccine (or the antisera which it elicits) may be for either a "prophylactic" or "therapeutic" purpose. When provided prophylactically, the vaccine is provided in advance of any symptom of C. difficile infection. The prophylactic administration of the vaccine serves to prevent or attenuate any subsequent infection. When provided therapeutically, the vaccine is provided upon the detection of a symptom of actual infection. The therapeutic administration of the vaccine serves to attenuate any actual infection. In some embodiments, administration of the vaccine of the invention attenuates C. difficile colonization and disease in the subject. In some embodiments, administration of the vaccine of the invention prevents C. difficile colonization and disease in the subject.

The vaccines (or antisera which it elicits) can be provided either prior to the onset of infection (so as to prevent or attenuate an anticipated infection) or after the initiation of an actual infection.

In some embodiments, the vaccines are administered with other vaccines targeting other components of C. difficile. In some embodiments, the vaccines are administered in conjunction with vaccines comprising toxoid preparations of enterotoxins A (TcdA) and B (TcdB) of C. difficile.

In some embodiments, the subject is co-administered with agents used to treat C. difficile infection, such as metronidazole and/or vancomycin in conjunction with methods as described herein.

The invention also provides a method for inducing an immune response which comprises administering to a subject, suspected of being at risk for infection caused by C. difficile, an immunologically-effective amount of an antisera elicited from the exposure of a second individual to a vaccine of the invention, such that it provides host immunity to the infection.

The vaccine of the invention can be administered to mammals of any age. In some embodiments, the vaccines can be administered as a single dose or in a series including one or more boosters. In some embodiments, the time interval between the first and second vaccinations is one week, two weeks, three weeks, 1 month, 2 months, 3 months, 4 months, 5 months, 6 months, 7 months, 8 months, 9 months, 10 months, 11 months, one year, 1.5 years and two years. In some embodiments, two sequential booster immunizations are administered.

In some embodiments, the immunization schedule would involve a primary series of three immunizations with a spacing of 1-2 months between the doses. In some embodiments, a booster dose could be administered ~6-12 months later.

Conjugate Vaccines

In one aspect, the present invention is further directed to a conjugate vaccine comprising a *C. difficile* type IV pilin, an antigenic fragment or a variant thereof.

The conjugation can be either through chemical or genetic means. The genetic or chemical conjugation encompasses coupling the type IV pilin either through gene fusion or chemically to another entity, for example, using cross-linkers, to increase the immune response. Standard techniques and methods can be employed to make the conjugate vaccines of the invention.

In some embodiments, the *C. difficile* type IV pilin, antigenic fragment or variant thereof is conjugated to another *C. difficile* type W pilin, antigenic fragment or variant thereof. In some embodiments, conjugation is to a bacterial toxin. In some embodiments, it is conjugated to a nontoxic variant of a bacterial toxin. In some embodiments, it is conjugated to a nontoxic variant of enterotoxin A (TcdA) or B (TcdB). Other toxins include tetanospasmin, alpha toxin, enterotoxin, botox diphtheria toxin, anthrax toxin, listeriolysin O, streptolysin, leukocidin (Panton-Valentine leukocidin), *Staphylococcus aureus* alpha/beta/delta, exfoliatin, toxic shock syndrome toxin, SEB), cord factor, diphtheria toxin, shiga toxin, verotoxin/shiga-like toxin *E. coli*), *E. coli* heat-stable enterotoxin/enterotoxin, cholera toxin, pertussis toxin, *Pseudomonas* exotoxinextracellular adenylate cyclase, type I (Superantigen), type II (Pore forming toxins), type III (AB toxin/AB5), lipopolysaccharide (Lipid A), *Bacillus thuringiensis* delta endotoxin, clumping factor A, and fibronectin binding protein A.

In some embodiments, the *C. difficile* type IV pilin, antigenic fragment or variant thereof conjugated to a bacterial toxin is selected from the group consisting of PilA1, PilA2, PilA3 and PilA4. In some embodiments, the *C. difficile* type IV pilin, antigenic fragment or variant thereof conjugated to a bacterial toxin is PilA2.

In some embodiments, a *C. difficile* type IV pilin, antigenic fragment or variant thereof is conjugated to a polysaccharide, using techniques known in the art.

A multivalent vaccine may also be prepared by mixing the *C. difficile* type IV pilin conjugate with other antigens, including other *C. difficile* type IV pilins and conjugates thereof, other *C. difficile* antigens and conjugates thereof, antigens against other organisms and conjugates thereof, bacterial toxins as discussed above and conjugates thereof, and/or other polysaccharides and conjugates thereof, using techniques known in the art. In some embodiments, the invention is directed to a multivalent vaccine comprising a mixture of *C. difficile* type IV pilin conjugates derived from various *C. difficile* strains, each conjugate comprising a type N pilin characteristic of the strain.

Methods for making conjugate vaccines are described in, for example, US Patent Application Publication No, 20090028889. Techniques to conjugate a type N pilin include, in part, coupling through available functional groups (such as amino, carboxyl, thio and aldehyde groups). See, e.g., Hermanson, Bioconjugate Techniques (Academic Press; 1992); Aslam and Dent, eds. Bioconjugation: Protein coupling Techniques for the Biomedical Sciences (MacMillan: 1998); S. S. Wong, *Chemistry of Protein Conjugate and Crosslinking CRC Press* (1991), and Brenkeley et al., Brief Survey of Methods for Preparing Protein Conjugates With Dyes, Haptens and Cross-Linking Agents, *Bioconjugate Chemistry* 3 #1 (January 1992); Jacob, C. O, et al., *Eur. J. Immunol.* 16:1057-1062 (1986); Parker, J. M. R. et al., In: *Modern Approaches to Vaccines*, Chanock, R. M. et al., eds, pp. 133-138, Cold Spring Harbor Laboratory, Cold Spring Harbor, N.Y. (1983); Zurawski, V. R, et al., *J. Immunol.* 121: 122-129 (1978); Klipstein, F. A, et al., *Infect. Immun.* 37:550-557 (1982); Bessler, W. G, *Immunobiol.* 170:239-244 (1985); Posnett, D. N, et al., *J. Biol. Chem.* 263:1719-1725 (1988); Ghose, A. C, et al., *Molec. Immunol.* 25:223-230 (1988); all of which disclosures are incorporated herein by reference). An example of a conjugate vaccine was developed against *Haemophilus influenzae* (Anderson, P, Infec. and *Immunology* 39:223-238 (1983); Chu, C, et al., *Infect. Immun.* 40:245-256 (1983); Lepow, M, *Pediat. Infect. Dis. J.* 6:804-807 (1987), which disclosures are incorporated herein by reference), Additional methods for producing such a conjugate vaccine are disclosed by European Patent Publication 245, 045; U.S. Pat. Nos. 4,673,574 and 4,761,283; U.S. Pat. No. 4,789,735; European Patent Publication No. 206,852; U.S. Pat. No. 4,619,828; U.S. Pat. No. 4,284,537; U.S. Pat. No. 5,192,540; U.S. Pat. No. 5,370,872; U.S. Pat. No. 5,302,386; and U.S. Pat. No. 5,576,002 all of which disclosures are incorporated herein by reference.

In some embodiments, the conjugate vaccine comprises a type IV pilin, antigenic fragment or a variant thereof selected from the group consisting of PilA1, PilA2, PilA3 and PilA4.

In some embodiments, the conjugate vaccine comprises a combination of type IV pilins, antigenic fragments or variants thereof as described herein.

In some embodiments, the conjugate vaccine comprises multiple alleles of a type IV pilin, antigenic fragment or variant thereof in combinations as described herein. For example, in some embodiments, multiple alleles are genetically conjugated to each other to make a fusion protein. In some embodiments, the conjugate vaccine comprises PilA1.1, PilA1.2, PilA1.3, PilA1.4 and PilA1.5 or antigenic fragments or variants thereof. In some embodiments, the conjugate vaccine comprises PilA2.1 and PilA2.2 or antigenic fragments or variants thereof. In some embodiments, the conjugate vaccine comprises PilA3.1, PilA3.2 and PilA3.3 or antigenic fragments or variants thereof.

Vaccine Compositions

As would be understood by one of ordinary skill in the art, when the *C. difficile* type IV pilin of the present invention is provided to a subject, it may be in a composition which may contain salts, buffers, adjuvants, or other substances which are desirable for improving the efficacy of the composition. Adjuvants are substances that can be used to specifically augment a specific immune response. Normally, the adjuvant and the composition are mixed prior to presentation to the immune system, or presented separately, but into the same site of the animal being immunized. Adjuvants can be loosely divided into several groups based upon their composition. These groups include oil adjuvants (for example, Freund's complete and incomplete), mineral salts (for example, AlK $(SO_4)_2$, AlNa$(SO_4)_2$, AlNH$_4$ $(SO_4)$, silica, kaolin, and carbon), polynucleotides (for example, poly IC and poly AU acids), and certain natural substances (for example, wax D from *Mycobacterium tuberculosis*, as well as substances found in *Corynebacterium parvum*, or *Bordetella pertussis*, and members of the genus *Brucella*. Adjuvants are described by Warren et al. (*Ann. Rev. Biochem.*, 4:369-388, 1986), the entire disclosure of which is hereby incorporated by reference.

In some embodiments of the invention, conventional adjuvants can be administered together with the type IV pilin. In some embodiments, the adjuvants are saponins such as, for example, Quil A. (Superfos A/S, Denmark). In some embodiments, monophosphoryl lipid A plus trehalose dimycolate (Ribi-700; Ribi Immunochemical Research, Hamilton, Mont.) is used as an adjuvant.

The vaccines can be formulated into liquid preparations for, e.g., nasal, rectal, buccal, vaginal, peroral, intragastric, mucosal, perlinqual, alveolar, gingival, olfactory, or respiratory mucosa administration. Suitable forms for such administration include solutions, suspensions, emulsions, syrups, and elixirs. The vaccines can also be formulated for parenteral, subcutaneous, intradermal, intramuscular, intraperitoneal or intravenous administration, injectable administration, sustained release from implants, or administration by eye drops. Suitable forms for such administration include sterile suspensions and emulsions. Such vaccines can be in admixture with a suitable carrier, diluent, or excipient such as sterile water, physiological saline, glucose, and the like. The vaccines can also be lyophilized. The vaccines can contain auxiliary substances such as wetting or emulsifying agents, pH buffering agents, gelling or viscosity enhancing additives, preservatives, flavoring agents, colors, and the like, depending upon the route of administration and the preparation desired. Texts, such as *Remington: The Science and Practice of Pharmacy*, Lippincott Williams & Wilkins; 20th edition (Jun. 1, 2003) and *Remington's Pharmaceutical Sciences*, Mack Pub. Co.; $18^{th}$ and $19^{th}$ editions (December 1985, and June 1990, respectively), incorporated herein by reference in their entirety, can be consulted to prepare suitable preparations. Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. The presence of such additional components can influence the physical state, solubility, stability, rate of in vivo release, and rate of in vivo clearance, and are thus chosen according to the intended application, such that the characteristics of the carrier are tailored to the selected route of administration.

In some embodiments, the vaccine of the invention is administered parenterally. Parenteral vehicles include phosphate buffered saline, sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. In some embodiments, the vaccines for parenteral administration may be in the form of a sterile injectable preparation, such as a sterile injectable aqueous or nonaqueous solutions, suspensions, and emulsions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Suspensions may be formulated according to methods well known in the art using suitable dispersing or wetting agents and suspending agents. The sterile injectable preparation may also be a sterile injectable solution or suspension in a parenterally acceptable diluent or solvent, such as a solution in 1,3-butanediol. Suitable diluents include, for example, water, Ringer's solution and isotonic sodium chloride solution. In addition, sterile fixed oils may be employed conventionally as a solvent or suspending medium. For this purpose, any bland fixed oil may be employed including synthetic mono- or diglycerides. In addition, fatty acids such as oleic acid may likewise be used in the preparation of injectable preparations.

Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

In some embodiments, the vaccines are provided as liquid suspensions or as freeze-dried products. Suitable liquid preparations include, e.g., isotonic aqueous solutions, suspensions, emulsions, or viscous compositions that are buffered to a selected pH. Transdermal preparations include lotions, gels, sprays, ointments or other suitable techniques. If nasal or respiratory (mucosal) administration is desired (e.g., aerosol inhalation or insufflation), compositions can be in a form and dispensed by a squeeze spray dispenser, pump dispenser or aerosol dispenser. Aerosols are usually under pressure by means of a hydrocarbon. Pump dispensers can preferably dispense a metered dose or a dose having a particular particle size, as discussed below.

When in the form of solutions, suspensions and gels, in some embodiments, the formulations contain a major amount of water (preferably purified water) in addition to the active ingredient. Minor amounts of other ingredients such as pH adjusters, emulsifiers, dispersing agents, buffering agents, preservatives, wetting agents, jelling agents, colors, and the like can also be present.

In some embodiments, the compositions are isotonic with the blood or other body fluid of the recipient. In some embodiments, the isotonicity of the compositions can be attained using sodium tartrate, propylene glycol or other inorganic or organic solutes. In some embodiments, sodium chloride is used. In some embodiments, buffering agents can be employed, such as acetic acid and salts, citric acid and salts, boric acid and salts, and phosphoric acid and salts. In some embodiments of the invention, phosphate buffered saline is used for suspension.

In some embodiments, the viscosity of the compositions can be maintained at the selected level using a pharmaceutically acceptable thickening agent. In some embodiments, methylcellulose is used because it is readily and economically available and is easy to work with. Other suitable thickening agents include, for example, xanthan gum, carboxymethyl cellulose, hydroxypropyl cellulose, carbomer, and the like. The concentration of the thickener can depend upon the agent selected. In some embodiments, viscous compositions are prepared from solutions by the addition of such thickening agents.

In some embodiments, a pharmaceutically acceptable preservative can be employed to increase the shelf life of the compositions. Benzyl alcohol can be suitable, although a variety of preservatives including, for example, parabens, thimerosal, chlorobutanol, or benzalkonium chloride can also be employed. A suitable concentration of the preservative can be from 0.02% to 2% based on the total weight although there can be appreciable variation depending upon the agent selected.

In some embodiments, pulmonary delivery of the vaccine can also be employed. In some embodiments, the vaccine is delivered to the lungs of a mammal while inhaling and traverses across the lung epithelial lining to the blood stream. A wide range of mechanical devices designed for pulmonary delivery of therapeutic products can be employed, including but not limited to nebulizers, metered dose inhalers, and powder inhalers, all of which are familiar to those skilled in the art. These devices employ formulations suitable for the dispensing of the conjugate. Typically, each formulation is specific to the type of device employed and can involve the use of an appropriate propellant material, in addition to diluents, adjuvants and/or carriers useful in therapy.

In embodiments where the vaccine is prepared for pulmonary delivery in particulate form, it has an average particle size of from 0.1 μm or less to 10 μm or more. In some embodiments, it has an average particle size of from about 0.2, 0.3, 0.4, 0.5, 0.6, 0.7, 0.8, or 0.9 μm to about 1.0, 1.5, 2.0, 2.5, 3.0, 3.5, 4.0, 4.5, 5.0, 5.5, 6.0, 6.5, 7.0, 7.5, 8.0, 8.5, 9.0, or 9.5 μm for pulmonary delivery. Pharmaceutically acceptable carriers for pulmonary delivery of the vaccine include carbohydrates such as trehalose, mannitol, xylitol, sucrose, lactose, and sorbitol. Other ingredients for use in formulations can include DPPC, DOPE, DSPC and DOPC. Natural or synthetic surfactants can be used, including polyethylene glycol and dextrans, such as cyclodextran and other related enhancers, as well as cellulose and cellulose derivatives, and amino acids can also be used. Liposomes, microcapsules, microspheres, inclusion complexes, and other types of carriers can also be employed.

Formulations suitable for use with a nebulizer, either jet or ultrasonic, typically comprise the peptide dissolved or suspended in water at a concentration of about 0.01 or less to 100 mg or more of peptide per mL of solution, preferably from about 0.1, 1, 2, 3, 4, 5, 6, 7, 8, 9, or 10 mg to about 15, 20, 25, 30, 35, 40, 45, 50, 55, 60, 65, 70, 75, 80, 85, or 90 mg of peptide per mL of solution. The formulation can also include a buffer and a simple sugar (e.g., for protein stabilization and regulation of osmotic pressure). The nebulizer formulation can also contain a surfactant, to reduce or prevent surface induced aggregation of the conjugate caused by atomization of the solution in forming the aerosol.

Formulations for use with a metered-dose inhaler device generally comprise a finely divided powder containing the inventive compound suspended in a propellant with the aid of a surfactant. The propellant can include conventional propellants, such chlorofluorocarbon, a hydrochlorofluorocarbons, hydrofluorocarbons, and hydrocarbons, such as trichlorofluoromethane, dichlorodifluoromethane, dichlorotetrafluoroethanol, and 1,1,1,2-tetrafluoroethane, and combinations thereof. Suitable surfactants include sorbitan trioleate, soya lecithin, and oleic acid.

Formulations for dispensing from a powder inhaler device typically comprise a finely divided dry powder containing the peptide, optionally including a bulking agent, such as lactose, sorbitol, sucrose, mannitol, trehalose, or xylitol in an amount that facilitates dispersal of the powder from the device, typically from about 1 wt. % or less to 99 wt. % or more of the formulation, preferably from about 5, 10, 15, 20, 25, 30, 35, 40, 45, or 50 wt. % to about 55, 60, 65, 70, 75, 80, 85, or 90 wt. % of the formulation.

Diagnostic Methods

In some embodiments, the invention relates to type IV pilin polynucleotides, proteins or antibodies reactive specifically against the type IV pilins for use as diagnostic reagents. Detection of DNA, mRNA (or cDNA), protein levels, or antibodies directed against type IV pilins will provide a diagnostic tool that can add to or define a diagnosis of infection or susceptibility to infection. In some embodiments, the detection of one or more type IV pilins will direct the medical practitioner to set an appropriate course of treatment for the patient.

Nucleic acids for diagnosis may be obtained, for example, from a subject's bodily sample, such as, for example, the stool. Nucleic acid levels (DNA, mRNA, cDNA) can be assayed by comparison to a standard or control level from an uninfected and/or infected individual. The nucleic acids can be used directly for detection or can amplified enzymatically by using PCR or other amplification techniques prior to analysis.

In some embodiments, expression is measured at the RNA level using any of the methods well known in the art for the quantitation of polynucleotides; for example, RT-PCR, RNase protection, Northern blotting, array analysis, and other hybridization methods may be utilized. Assay techniques that may be used to determine the level of a type IV pilin protein in a sample derived from a host include radioimmunoassays, competitive-binding assays, Western blot analysis and ELISA assays.

In some embodiments, the invention is directed to methods for detecting *C. difficile* infection in a subject. In some embodiments, the method comprises obtaining a bodily sample from the subject; and analyzing the sample for the presence of a type IV pilin from *C. difficile* or an antibody that binds thereto. In some embodiments, the sample is a stool sample, a blood sample, a serum sample, a urine sample, and a saliva sample.

In some embodiments, the type IV pilin nucleic acid is detected. In some embodiments, type IV pilin protein is detected. In some embodiments, an antibody binding to type IV pilin is detected.

Other *C. difficile* markers, such as enterotoxins A (TcdA) and B (TcdB), can also be simultaneously assayed, in accordance with the methods of the present invention.

Type IV Pilin Antibodies

The type IV pilins of the invention or their antigenic fragments or variants thereof, or cells expressing them may also be used as immunogens to produce antibodies immunospecific for the type IV pilin.

Antibodies generated against the type IV pilin polypeptides can be obtained by administering the polypeptides or antigenic fragments, variants or cells to an animal using routine protocols. In some embodiments, antisera against type IV pilin are generated in a subject for use in passive immunotherapy. For preparation of monoclonal antibodies, any technique which provides antibodies produced by continuous cell line cultures can be used. Examples include the hybridoma technique (Kohler, G. and Milstein, C., *Nature* 256:495-497 (1975)), the trioma technique, the human B-cell hybridoma technique (Kozbor, et al., *Immunology Today* 4:72 (1983)) and the EBV-hybridoma technique (Cole et al., *Monoclonal Antibodies and Cancer Therapy*, pp. 77-96, Alan R. Liss, Inc., (1985)).

Techniques for the production of single chain antibodies (U.S. Pat. No. 4,946,778) may also be adapted to produce single chain antibodies to polypeptides of this invention. Also, transgenic mice, or other organisms including other mammals, may be used to express humanized antibodies. In some embodiments, the antibodies are humanized.

In some embodiments, the above-described antibodies or antisera is employed to detect a type IV pilin, for use in passive immunotherapy, or to purify a type IV pilin by affinity chromatography.

The present invention is further illustrated by the following Examples. These Examples are provided to aid in the understanding of the invention and are not to be construed as a limitation thereof.

Example 1

Expression and purification of the type IV pilins from *C. difficile*. We used the following novel strategy to express and purify high levels of recombinant *C. difficile* type IV pilins. This method involves identification of insoluble and soluble domains of the proteins, engineering of codon optimized synthetic pilin genes which do not exist in nature but which result in expression of pilin domains identical to those found in nature, optimal expression of pilin proteins, and purification to homogeneity. This method has been successful using two different pilin gene sequences.

We used our understanding of type IV pilin protein structure to identify the pre-pilin peptidase cleavage sites and hydrophobic mature amino-termini of each pilin gene. For the pilA2 gene found in *C. difficile* strain 630 and 10 other sequenced strains, we omitted from the recombinant construct the codons for the signal sequence and the first 27 residues of the mature protein (FIG. 1). In type IV pilus biogenesis the former domain is removed prior to pilus assembly and the latter domain is highly hydrophobic, buried in the core of the pilus, and interferes with pilin solubility and purification. Antibodies directed against this domain are not protective against infection since they do not bind to epitopes expressed on the pilus surface.

Figure 2:
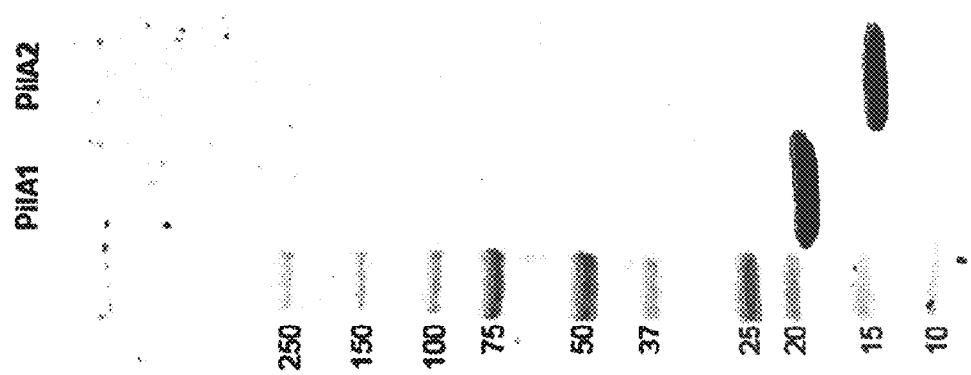

Next, using oligonucleotide assembly polymerase chain reaction, we synthesized the remaining part of the pilA2 gene using codons optimized for *E. coli* to avoid translation limitations imposed by the differences in codon preference between these unrelated species. This procedure resulted in alteration of 73% of the codons without changing any of the natural amino acid sequence. This sequence is entirely novel and does not occur in nature. We then cloned the truncated optimized pilA2 gene into the pET30 T7 expression plasmid (Novagen) in frame with a hexahistidine tag (facilitating purification) and an enterokinase cleavage site (for potential removal of the tag, if required). After transformation and induction in *E. coli* strain BL21, we achieved extraordinarily robust levels of expression of a protein with the expected molecular mass of 13.8 kDa (FIG. 2). We were able to obtain more than 70 mg of pure protein from two liters of culture after one-step affinity purification on a nickel-nitrilotriacetic acid column.

Similarly, we engineered, synthesized and subcloned a recombinant pilA1 expression plasmid using the sequence from *C. difficile* strain 630 as a guide and following the identical strategy of domain omission, codon optimization, and vector and strain selection used for pilA2. We were similarly successful in high yield, high purity expression of recombinant PilA1 protein (FIG. 2). In the sequence listing we present the sequence of novel recombinant vectors for expression of each variant of PilA1, PilA2, PilA3, and PilA4. In some embodiments, the invention relates to identifying, engineering and producing recombinant synthetic *C. difficile* pilin genes of any type for pilin protein purification and use in vaccines and for diagnosis.

Example 2

Figure 3:
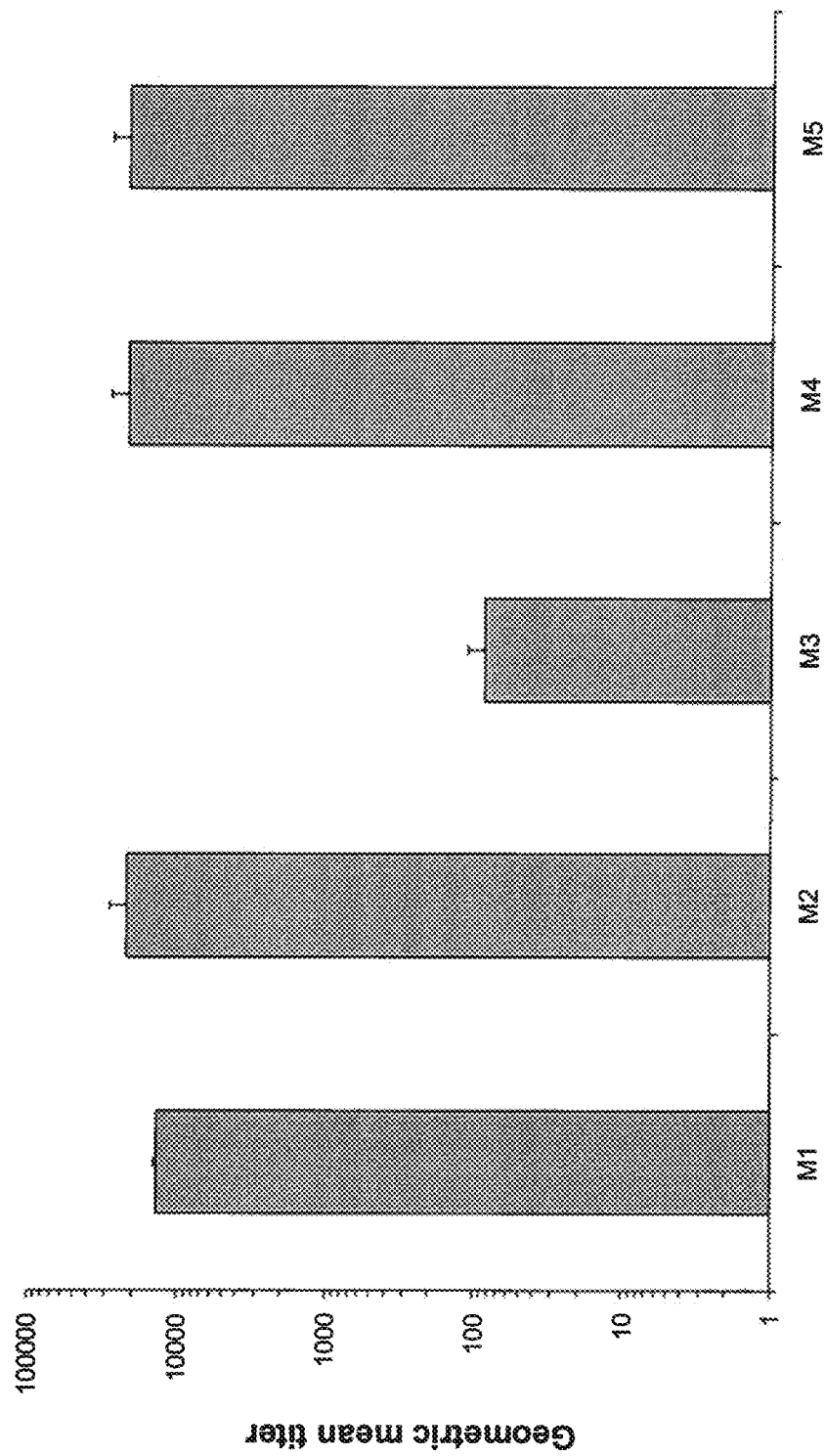

Generation of polyclonal antisera against recombinant *C. difficile* PilA1. We immunized 5 mice each with purified PilA1 and PilA2 pilin proteins using a standard regimen consisting of primary subcutaneous injection with Freund's complete adjuvant followed by two booster immunizations with incomplete adjuvant. Using the purified pilin proteins as antigens, we were able to demonstrate in 4 of 5 mice a significant immune response against PilA1 (FIG. 3). However, PilA2 was not immunogenic using this protocol.

Example 3

The efficacy of passive immunization with antibodies to PilA1 in prevention of *C. difficile* colonization and disease in a murine model. We will determine the efficacy of passive immunization using a recently reported murine model of experimental *C. difficile* colitis. Chen et al. *Gastroenterol.* 135(6):1984-92 (2008). Female nine-week-old C57BL6 mice will be treated for 3 days with an antibiotic cocktail of kanamycin (0.4 mg/ml), gentamicin (0.035 mg/ml), colistin (850 U/ml), metronidazole (0.215 mg/ml), and vancomycin (0.045 mg/ml), administered in the drinking water. After this treatment, mice will be switched over to regular drinking water for another 3 days. Finally, on day 7, a single dose of clindamycin (10 mg/kg) will be administered by the intraperitoneal route 24 hrs prior to orogastric challenge with *C. difficile* strain 630. One group of 14 mice will receive twice the $LD_{50}$ ($1\times10^4$ CFU) of *C. difficile* strain 630 pre-mixed with normal mouse sera and the other will receive the same dose pre-mixed with pooled immune sera from the four mice with titers against PilA1 greater than 1:10,000. Mice will be weighed daily, scored for the development of diarrhea, and followed until they recover, die or require euthanasia. CDAD will be defined as any of the following: diarrhea, loss of 5% of pre-challenge body weight, or death. The experiment will be repeated once. With 28 mice in each group there is an 80% chance of detecting a reduction in CDAD, the primary endpoint, from 60% to 20% with a P value<0.05. In addition to monitoring CDAD, we will measure the effect of passive immunization on colonization and excretion of the organism, which will be highly relevant to control of *C. difficile* in health care settings.

Example 4

The efficacy of immunization with purified pilin in prevention of *C. difficile* colonization and disease in a murine model. We will establish the immunogenicity and protective efficacy of immunization with PilA1 and PilA2 in the murine model. Groups of six mice each will receive subcutaneous injections of PBS, PilA1 or PilA2. Fourteen days after completion of the immunization schedule, mice will be treated with antimicrobials and challenged with twice the $LD_{50}$ ($1\times10^4$ CFU) of *C. difficile* strain 630 as described in section above. Mice will be weighed daily, scored for the development of diarrhea, and followed until they recover, die or require euthanasia. CDAD will be defined as any of the following: diarrhea, loss of 5% of pre-challenge body weight, or death. The experiment will be repeated three times for a total of 24 mice in each group. In addition to monitoring CDAD, we will measure the effect of passive immunization on colonization and excretion of the organism.

What is claimed is:

1. An immunogenic composition comprising an isolated polypeptide comprising i) a *C. difficile* type IV pilin or an antigenic fragment or variant thereof, and ii) an affinity tag sequence to facilitate purification, wherein the antigenic fragment or variant thereof comprises a polypeptide sequence that has at least 90% sequence identity to a polypeptide sequence selected from the group consisting of:
   a. amino acids 35-173 of SEQ ID NO:2;
   b. amino acids 35-173 of SEQ ID NO:6;
   c. amino acids 35-173 of SEQ ID NO:10;
   d. amino acids 35-171 of SEQ ID NO:14;
   e. amino acids 35-170 of SEQ ID NO:18;
   f. amino acids 34-119 of SEQ ID NO:22;
   g. amino acids 31-116 of SEQ ID NO:26;
   h. amino acids 32-164 of SEQ ID NO:30;
   i. amino acids 32-164 of SEQ ID NO:34;
   j. amino acids 32-162 of SEQ ID NO:38;
   k. amino acids 36-272 of SEQ ID NO:42;
   l. SEQ ID NO:2;
   m. SEQ ID NO:6;
   n. SEQ ID NO:10;
   o. SEQ ID NO:14;
   p. SEQ ID NO:18;
   q. SEQ ID NO:22;
   r. SEQ ID NO:26;
   s. SEQ ID NO:30;
   t. SEQ ID NO:34; and
   u. SEQ ID NO:38.

2. The composition of claim 1, comprising a combination of the isolated polypeptides.

3. The composition of claim 2, wherein said isolated polypeptides are conjugated.

4. The composition of claim 2, wherein said isolated polypeptides are conjugated genetically to form a fusion protein, wherein the fusion protein is produced from a nucleic acid sequence encoding the combination.

5. The composition of claim 2, wherein the combination of isolated polypeptides comprises a *C. difficile* type IV pilin selected from the group consisting of:
   a. SEQ ID NO:2;
   b. SEQ ID NO:6;
   c. SEQ ID NO:10;
   d. SEQ ID NO:14;
   e. SEQ ID NO:18;
   f. SEQ ID NO:22;
   g. SEQ ID NO:26;
   h. SEQ ID NO:30;
   i. SEQ ID NO:34;
   j. SEQ ID NO:38;
   k. SEQ ID NO:42; and
   l. combinations thereof.

6. The composition of claim 2, wherein the combination of isolated polypeptides comprises a *C. difficile* type IV pilin antigenic fragment, wherein the antigenic fragment comprises a polypeptide sequence selected from the group consisting of:
   a. amino acids 35-173 of SEQ ID NO:2;
   b. amino acids 35-173 of SEQ ID NO:6;
   c. amino acids 35-173 of SEQ ID NO:10;
   d. amino acids 35-171 of SEQ ID NO:14;
   e. amino acids 35-170 of SEQ ID NO:18;
   f. amino acids 34-119 of SEQ ID NO:22;
   g. amino acids 31-116 of SEQ ID NO:26;
   h. amino acids 32-164 of SEQ ID NO:30;
   i. amino acids 32-164 of SEQ ID NO:34;
   j. amino acids 32-162 of SEQ ID NO:38; and
   k. amino acids 36-272 of SEQ ID NO:42.

7. The composition of claim 6, wherein the antigenic fragment is recombinantly produced.

8. The composition of claim 7, wherein the antigenic fragment is produced in *E. coli*.

9. The composition of claim 8, wherein the polypeptide is encoded by a nucleic acid sequence optimized to increase expression in *E. coli* using codons that are preferred in *E. coli*, wherein the nucleic acid sequence is selected from the group consisting of:
   a. SEQ ID NO:3;
   b. SEQ ID NO:7;
   c. SEQ ID NO:11;
   d. SEQ ID NO:15;
   e. SEQ ID NO:19;
   f. SEQ ID NO:23;
   g. SEQ ID NO:27;
   h. SEQ ID NO:31;
   i. SEQ ID NO:35;
   j. SEQ ID NO:39; and
   k. SEQ ID NO:43.

10. The composition of claim 2, wherein the combination comprises SEQ ID NO:2 or an antigenic fragment thereof, wherein the antigenic fragment comprises amino acids 35-173 of SEQ ID NO:2.

11. The composition of claim 10, wherein the combination further comprises a type IV pilin selected from the group consisting of:
   a. SEQ ID NO:6;
   b. SEQ ID NO:10;
   c. SEQ ID NO:14;
   d. SEQ ID NO:18; and
   e. combinations thereof.

12. The composition of claim 11, wherein the polypeptide further comprises an enzymatic cleavage sequence.

* * * * *